United States Patent
Okada

(10) Patent No.: US 9,817,325 B2
(45) Date of Patent: Nov. 14, 2017

(54) BENZIDINE DERIVATIVE, METHOD FOR PRODUCING BENZIDINE DERIVATIVE, AND ELECTROPHOTOGRAPHIC PHOTOSENSITIVE MEMBER

(71) Applicant: KYOCERA Document Solutions Inc., Osaka (JP)

(72) Inventor: Hideki Okada, Osaka (JP)

(73) Assignee: KYOCERA Document Solutions Inc., Osaka (JP)

( * ) Notice: Subject to any disclaimer, the term of this patent is extended or adjusted under 35 U.S.C. 154(b) by 0 days.

(21) Appl. No.: 15/214,908

(22) Filed: Jul. 20, 2016

(65) Prior Publication Data
US 2017/0031251 A1    Feb. 2, 2017

(30) Foreign Application Priority Data
Jul. 29, 2015   (JP) ................. 2015-149468

(51) Int. Cl.
   *G03G 5/04*    (2006.01)
   *G03G 5/06*    (2006.01)
   *C07C 211/54*    (2006.01)

(52) U.S. Cl.
   CPC ......... *G03G 5/0614* (2013.01); *C07C 211/54* (2013.01); *G03G 5/0672* (2013.01); *G03G 5/0696* (2013.01)

(58) Field of Classification Search
   CPC .. G03G 5/0614; G03G 5/0672; G03G 5/0696; C07C 211/54
   See application file for complete search history.

(56) References Cited

U.S. PATENT DOCUMENTS

| | | |
|---|---|---|
| 5,804,344 A | 9/1998 | Mitsumori |
| 6,030,734 A | 2/2000 | Mitsumori |
| 2011/0299890 A1* | 12/2011 | Imanaka .............. G03G 15/162 399/174 |

FOREIGN PATENT DOCUMENTS

JP    H09-244278 A    9/1997

* cited by examiner

*Primary Examiner* — Thorl Chea
(74) *Attorney, Agent, or Firm* — Studebaker & Brackett PC

(57) ABSTRACT

A benzidine derivative is represented by general formula (1). In the general formula (1), $R_1$, $R_2$, $R_3$, $R_4$, $R_5$, $R_6$, $R_7$, $R_8$, $R_9$, and $R_{10}$ each represent, independently of one another, a hydrogen atom, a halogen atom, an optionally substituted alkyl group having a carbon number of at least 1 and no greater than 6, an optionally substituted alkoxy group having a carbon number of at least 1 and no greater than 6, or an (Continued)

optionally substituted aryl group having a carbon number of at least 6 and no greater than 14. n represents an integer of at least 0 and no greater than 2.
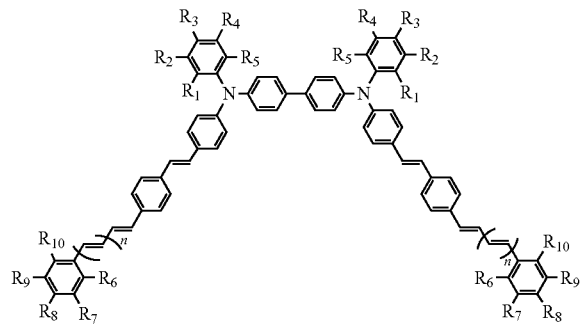
(1)
7 Claims, 4 Drawing Sheets

BENZIDINE DERIVATIVE, METHOD FOR PRODUCING BENZIDINE DERIVATIVE, AND ELECTROPHOTOGRAPHIC PHOTOSENSITIVE MEMBER

INCORPORATION BY REFERENCE

The present application claims priority under 35 U.S.C. §119 to Japanese Patent Application No. 2015-149468, filed on Jul. 29, 2015. The contents of this application are incorporated herein by reference in their entirety.

BACKGROUND

The present disclosure relates to a benzidine derivative, a method for producing a benzidine derivative, and an electrophotographic photosensitive member.

The electrophotographic photosensitive member is used in an electrophotographic image forming apparatus. The electrophotographic photosensitive member includes a photosensitive layer. The electrophotographic photosensitive member is for example a multi-layer electrophotographic photosensitive member or a single-layer electrophotographic photosensitive member. The multi-layer electrophotographic photosensitive member includes, as the photosensitive layer, a charge generating layer having a charge generating function and a charge transport layer having a charge transport function. The single-layer electrophotographic photosensitive member includes, as the photosensitive layer, a single-layer type photosensitive layer having a charge generation function and a charge transport function.

An example of the electrophotographic photosensitive member has a photosensitive layer containing an arylamine-based compound. An example of the arylamine-based compound is represented by chemical formula (HT-B).

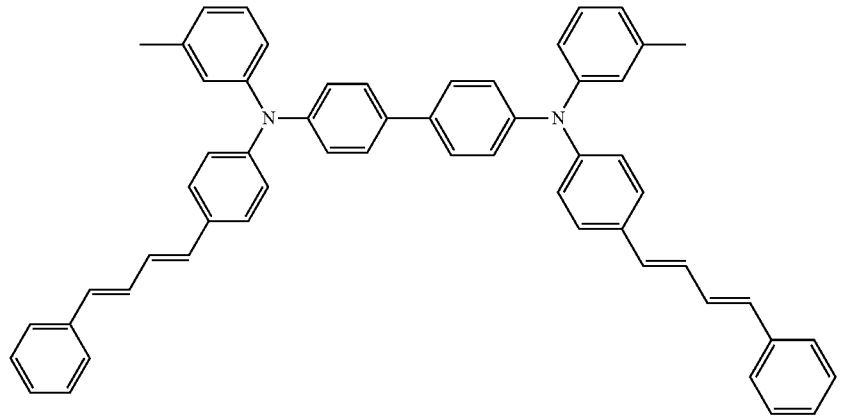

(HT-B)

SUMMARY

A benzidine derivative according to an aspect of the present disclosure is represented by general formula (1) shown below.

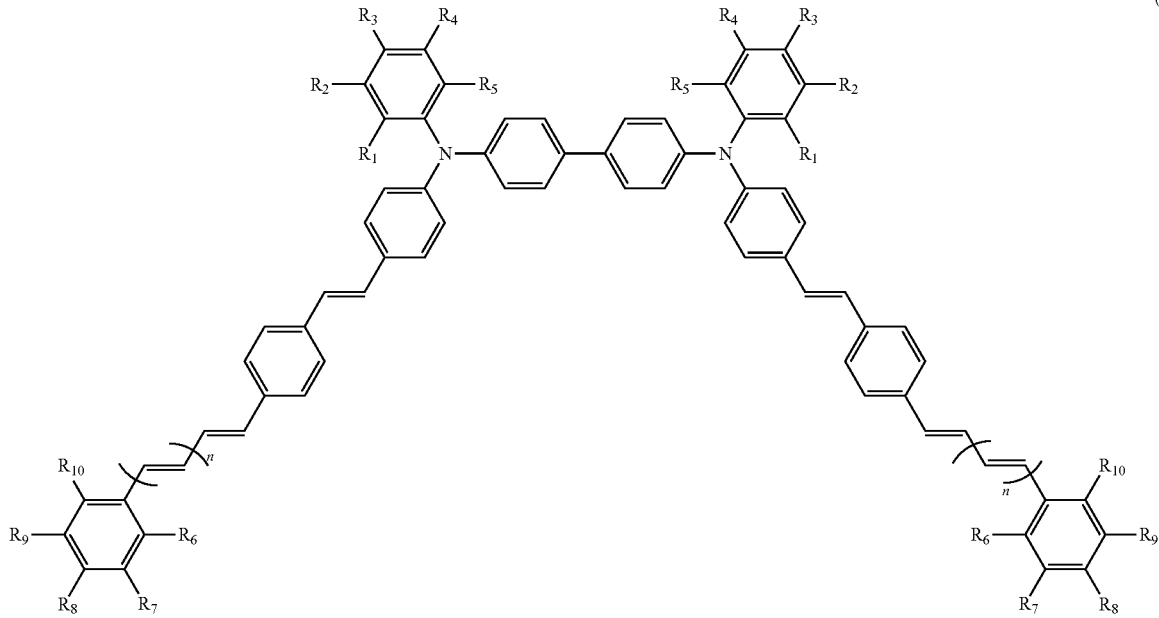

(1)

In the general formula (1), $R_1$, $R_2$, $R_3$, $R_4$, $R_5$, $R_6$, $R_7$, $R_8$, $R_9$, and $R_{10}$ each represent, independently of one another, a hydrogen atom, a halogen atom, an optionally substituted alkyl group having a carbon number of at least 1 and no greater than 6, an optionally substituted alkoxy group having a carbon number of at least 1 and no greater than 6, or an optionally substituted aryl group having a carbon number of at least 6 and no greater than 14, and n represents an integer of at least 0 and no greater than 2.

A method for producing a benzidine derivative according to another aspect of the present disclosure is a method for producing the above-described benzidine derivative. The method for producing the benzidine derivative according to the aspect of the present disclosure includes performing a reaction represented by scheme (R-6) shown below.

optionally substituted aryl group having a carbon number of at least 6 and no greater than 14. n represents an integer of at least 0 and no greater than 2. X represents a halogen atom.

An electrophotographic photosensitive member according to another aspect of the present disclosure includes a conductive substrate and a photosensitive layer. The photosensitive layer contains at least a charge generating material and the above-described benzidine derivative as a hole transport material.

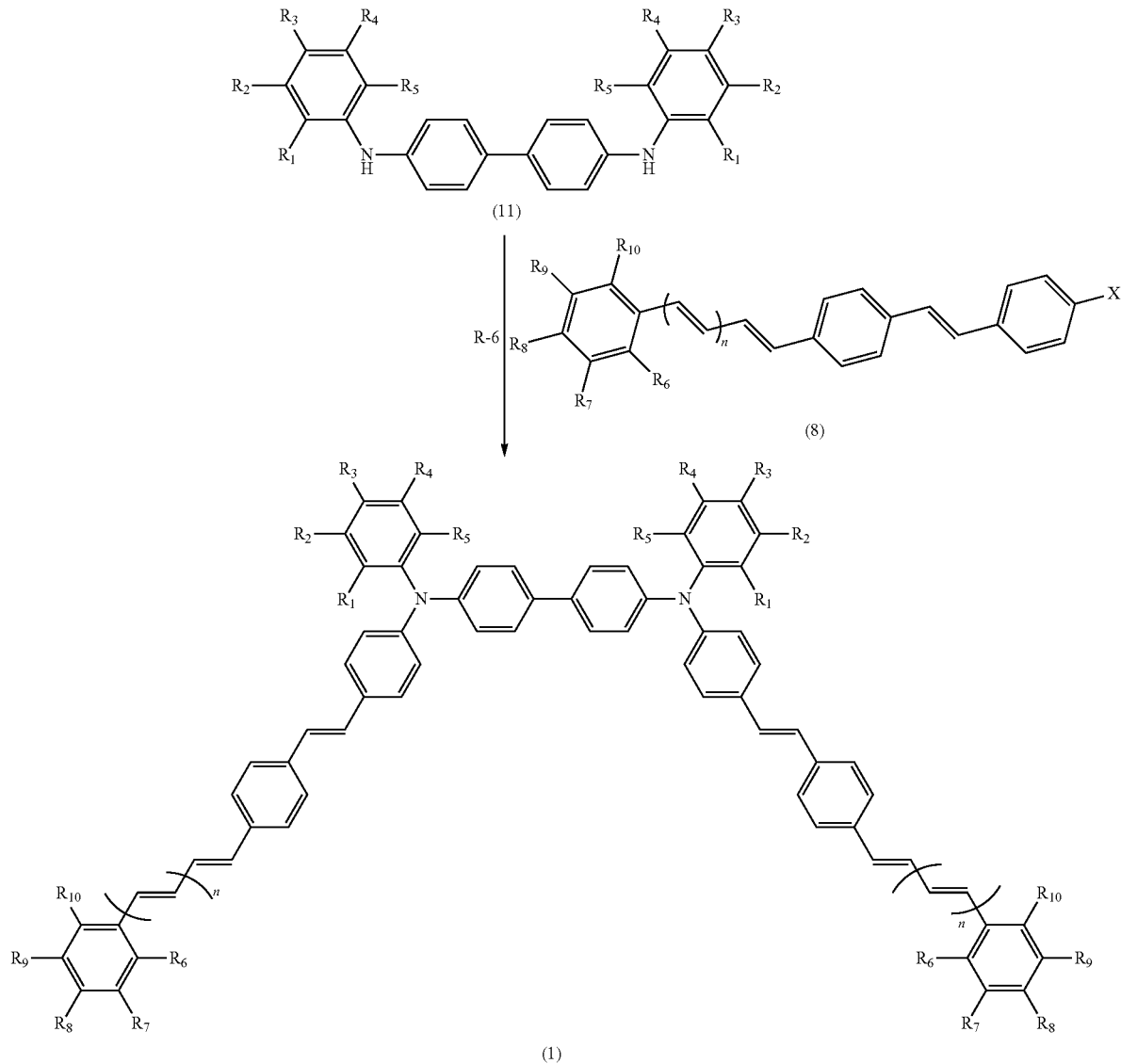

Figure 2:
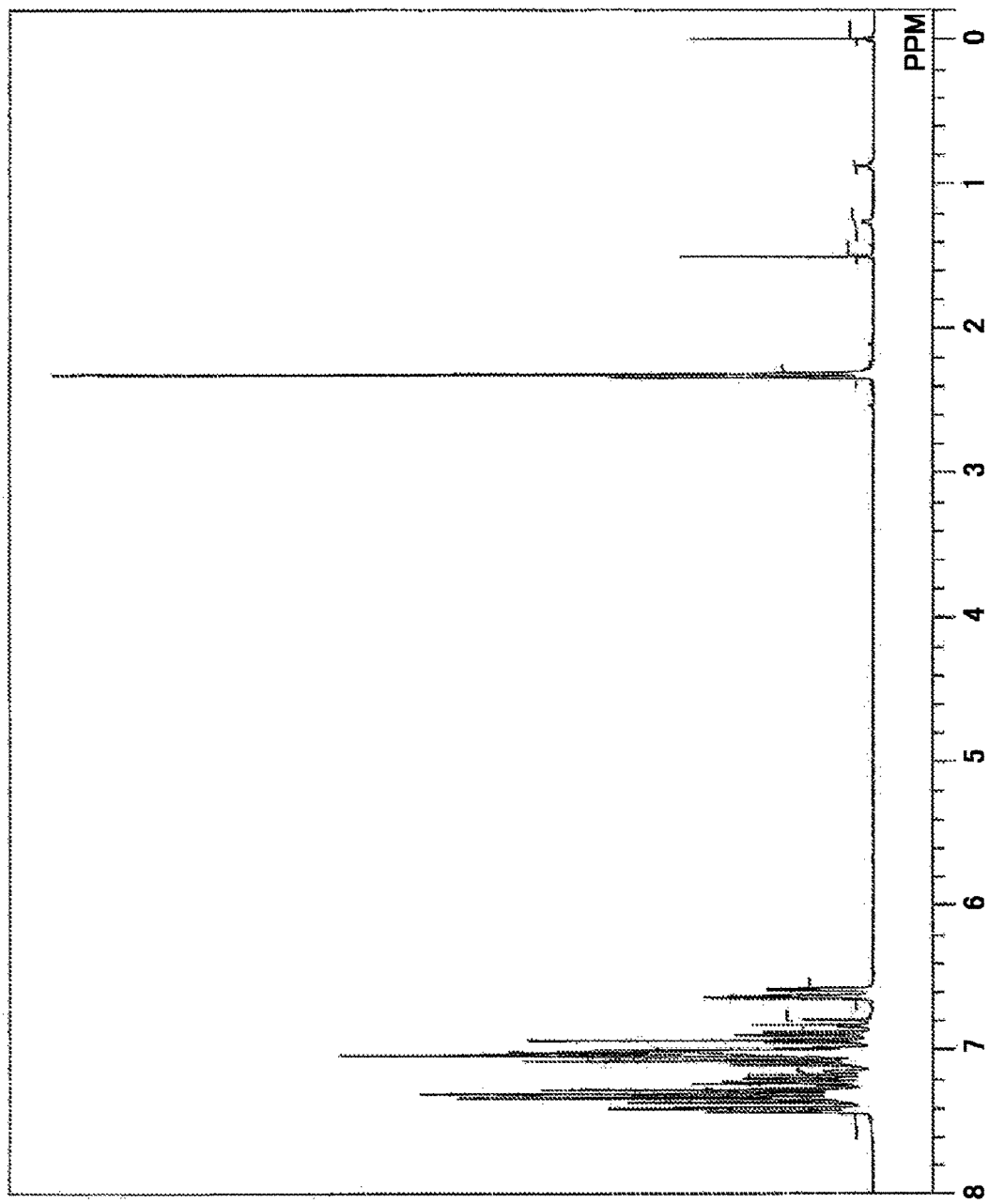

In the scheme (R-6), $R_1$, $R_2$, $R_3$, $R_4$, $R_5$, $R_6$, $R_7$, $R_8$, $R_9$, and $R_{10}$ each represent, independently of one another, a hydrogen atom, a halogen atom, an optionally substituted alkyl group having a carbon number of at least 1 and no greater than 6, an optionally substituted alkoxy group having a carbon number of at least 1 and no greater than 6, or an FIG. 2 is a $^1$H-NMR spectrum for a benzidine derivative represented by chemical formula (HT-3) according to the embodiment of the present disclosure.

Figure 3A:
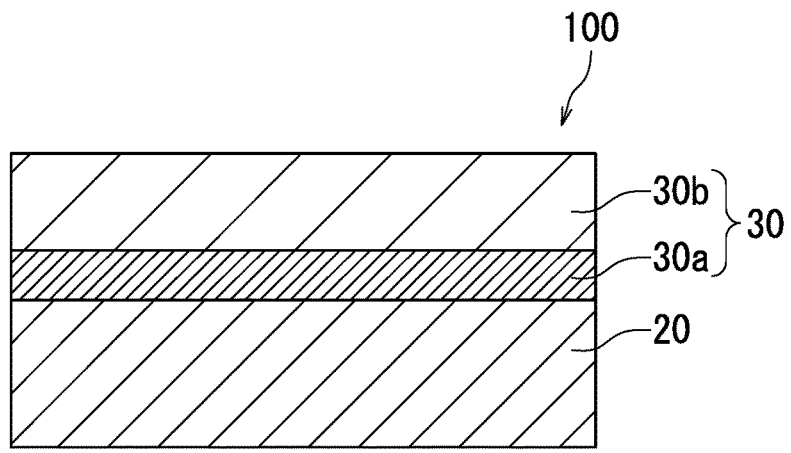
Figure 3B:
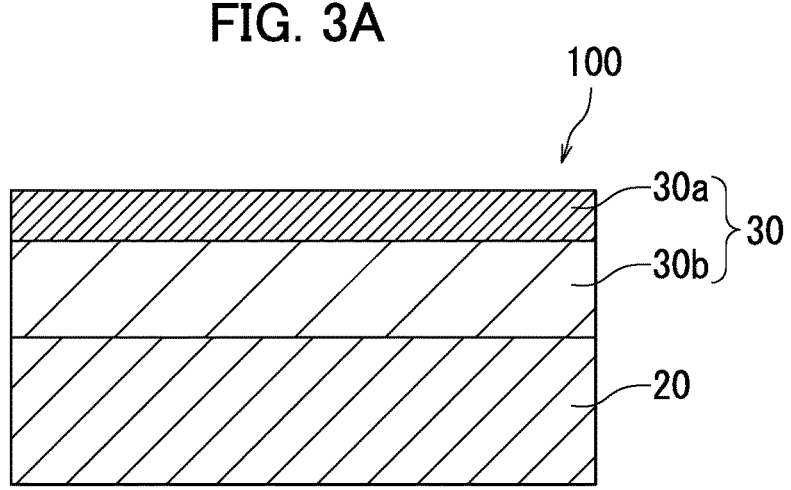
Figure 3C:
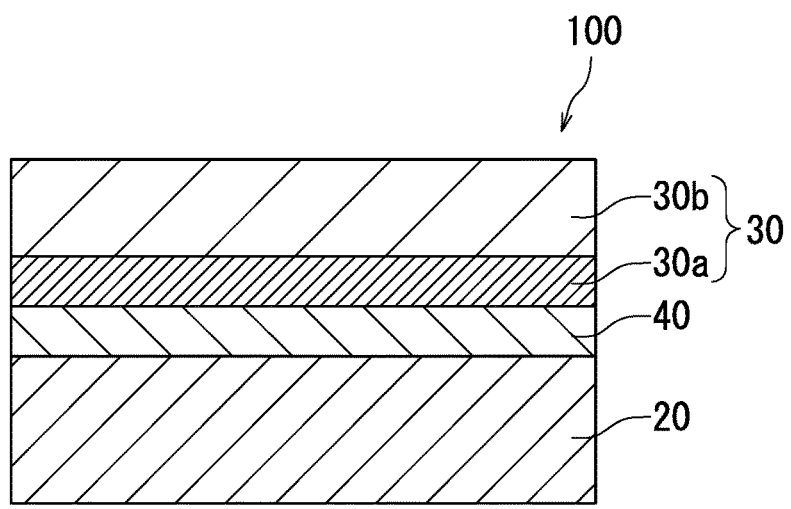

FIGS. 3A, 3B, and 3C are schematic cross sectional views each illustrating an example of an electrophotographic photosensitive member containing a benzidine derivative according to the embodiment of the present disclosure.

Figure 4A:
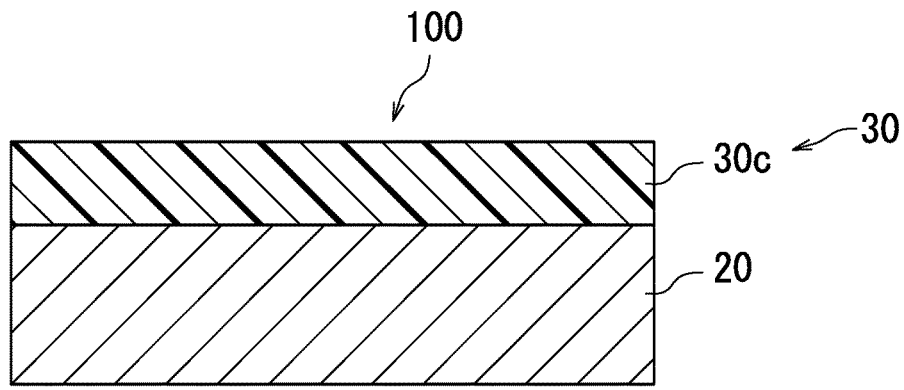
Figure 4B:
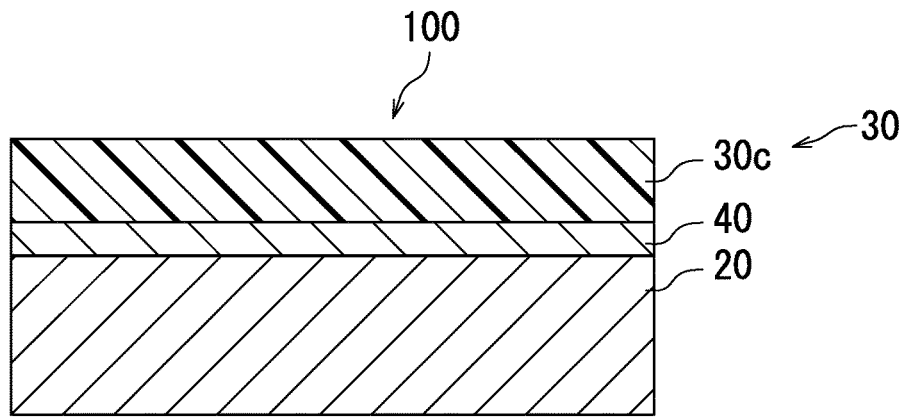
Figure 4C:
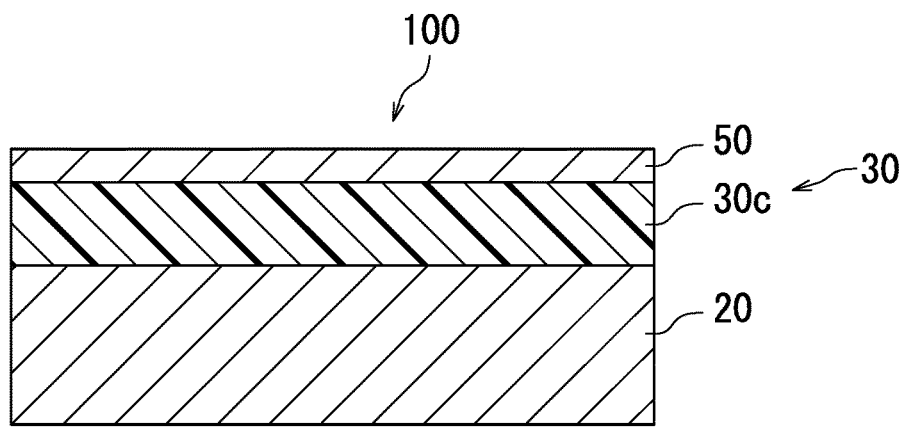

FIGS. 4A, 4B, and 4C are schematic cross sectional views each illustrating another example of the electrophotographic photosensitive member containing a benzidine derivative according to the embodiment of the present disclosure.

DETAILED DESCRIPTION

The following describes an embodiment of the present disclosure in detail. However, the present disclosure is not in any way limited by the embodiment described below. Appropriate variations may be made in practicing the present disclosure within the intended scope of the present disclosure. Although description is omitted as appropriate in some instances in order to avoid repetition, such omission does not limit the essence of the present disclosure.

Hereinafter, the term "-based" may be appended to the name of a chemical compound in order to form a generic name encompassing both the chemical compound itself and derivatives thereof. Also, when the term "-based" is appended to the name of a chemical compound used in the name of a polymer, the term indicates that a repeating unit of the polymer originates from the chemical compound or a derivative thereof. Compounds represented by general formulae or chemical formulae (2) to (11), (2a), (3a), (5a), (6a) to (6c), (7a) to (7c), (8a) to (8c), (9a) to (9e), (10a), and (11a) to (11c) may be respectively referred to as compounds 2 to 11, 2a, 3a, 5a, 6a to 6c, 7a to 7c, 8a to 8c, 9a to 9e, 10a, and 11a to 11c.

Hereinafter, unless otherwise stated, a halogen atom, an alkyl group having a carbon number of at least 1 and no greater than 6, an alkoxy group having a carbon number of at least 1 and no greater than 6, and an aryl group having a carbon number of at least 6 and no greater than 14 each mean the following.

A halogen atom as used herein is for example fluorine (fluoro group), chlorine (chloro group), or bromine (bromo group).

An alkyl group having a carbon number of at least 1 and no greater than 6 as used herein refers to an unsubstituted straight chain or branched chain alkyl group having a carbon number of at least 1 and no greater than 6. Examples of the alkyl group having a carbon number of at least 1 and no greater than 6 include a methyl group, an ethyl group, a propyl group, an isopropyl group, an n-butyl group, an s-butyl group, a t-butyl group, a pentyl group, an isopentyl group, a neopentyl group, and a hexyl group.

An alkoxy group having a carbon number of at least 1 and no greater than 6 as used herein refers to an unsubstituted straight chain or branched chain alkoxy group having a carbon number of at least 1 and no greater than 6. Examples of the alkoxy group having a carbon number of at least 1 and no greater than 6 include a methoxy group, an ethoxy group, an n-propoxy group, an isopropoxy group, an n-butoxy group, an s-butoxy group, a t-butoxy group, a pentyloxy group, an isopentyloxy group, a neopentyloxy group, and a hexyloxy group.

An aryl group having a carbon number of at least 6 and no greater than 14 as used herein is for example an unsubstituted monocyclic aromatic hydrocarbon group having a carbon number of at least 6 and no greater than 14, an unsubstituted fused bicyclic aromatic hydrocarbon group having a carbon number of at least 6 and no greater than 14, or an unsubstituted fused tricyclic aromatic hydrocarbon group having a carbon number of at least 6 and no greater than 14. Examples of the aryl group having a carbon number of at least 6 and no greater than 14 include a phenyl group, a naphthyl group, an anthryl group, and a phenanthryl group.

[Benzidine Derivative]

An embodiment of the present disclosure is directed to a benzidine derivative. The benzidine derivative according to the present embodiment is represented by general formula (1) shown below.

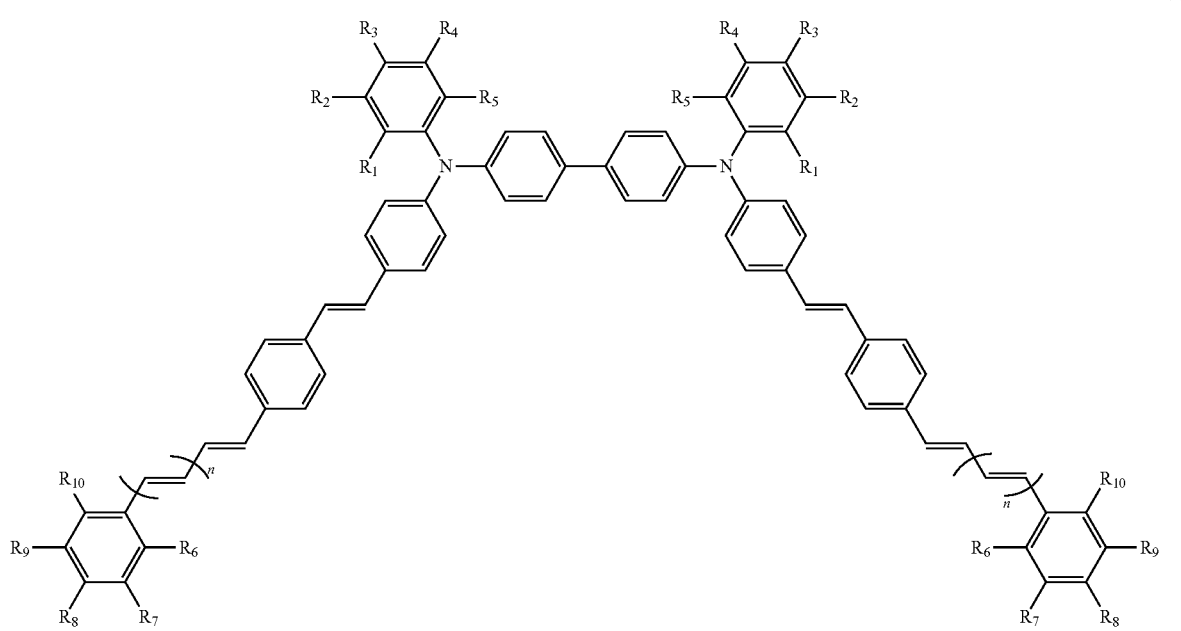

(1)

In the general formula (1), $R_1$, $R_2$, $R_3$, $R_4$, $R_5$, $R_6$, $R_7$, $R_8$, $R_9$, and $R_{10}$ each represent, independently of one another, a hydrogen atom, a halogen atom, an optionally substituted alkyl group having a carbon number of at least 1 and no greater than 6, an optionally substituted alkoxy group having a carbon number of at least 1 and no greater than 6, or an optionally substituted aryl group having a carbon number of at least 6 and no greater than 14. n represents an integer of at least 0 and no greater than 2.

The benzidine derivative represented by the general formula (1) (hereinafter, may be referred to as a benzidine derivative 1), when contained in a photosensitive layer of an electrophotographic photosensitive member (hereinafter, may be referred to simply as a photosensitive member), can inhibit crystallization in the photosensitive layer and improve electrical properties of the photosensitive member. Presumably, the reason therefore is as follows.

The benzidine derivative 1 has two nitrogen atoms. A phenyl group having $R_1$ to $R_5$ (short-chain conjugated group) and a group including a phenyl group having $R_6$ to $R_{10}$ (long-chain conjugated group) are bonded to each of the nitrogen atoms. It is thought that the benzidine derivative 1 having such a structure has the following advantages.

A first advantage is that the benzidine derivative 1 has an asymmetric structure as having the long-chain conjugated groups and the short-chain conjugated groups. Consequently, the benzidine derivative 1 is readily dissolved in a solvent that is used for photosensitive layer formation. Furthermore, the benzidine derivative 1 tends to be readily entangled with the chain structure of a binder resin as a result of the benzidine derivative 1 having the movable long-chain conjugated groups. It is therefore thought that compatibility between the benzidine derivative 1 and the binder resin is increased. Furthermore, the benzidine derivative 1 tends to form a stacking structure having an interplanar distance adjusted to a suitable distance as a result of the benzidine derivative 1 having the long-chain conjugated groups. For the reasons state above, it is thought that a photosensitive layer containing the benzidine derivative 1 tends not to experience crystallization.

A second advantage is that the benzidine derivative 1 has a moderately large molecular structure as having the long-chain conjugated groups. Consequently, a distance (hopping distance) between the π electron cloud of a molecule of the benzidine derivative 1 and the π electron cloud of another adjacent molecule of the benzidine derivative 1 that are present in the photosensitive layer tends to be small. It is thought that as a result, hole mobility between molecules of the benzidine derivative 1 is improved, and thus electrical properties of the photosensitive member is improved.

The alkyl group having a carbon number of at least 1 and no greater than 6 that is represented by $R_1$ to $R_{10}$ in the general formula (1) is preferably an alkyl group having a carbon number of at least 1 and no greater than 3, and more preferably a methyl group or an ethyl group. The alkyl group having a carbon number of at least 1 and no greater than 6 that is represented by $R_1$ to $R_{10}$ in the general formula (1) is optionally substituted. The alkyl group having a carbon number of at least 1 and no greater than 6 may for example have, as a substituent, a halogen atom, an alkoxy group having a carbon number of at least 1 and no greater than 6, or an aryl group having a carbon number of at least 6 and no greater than 14. The alkyl group having a carbon number of at least 1 and no greater than 6 preferably has an aryl group having a carbon number of at least 6 and no greater than 14 as a substituent, more preferably an monocyclic aromatic hydrocarbon group having a carbon number of at least 6 and no greater than 14, and particularly preferably a phenyl group. Although no particular limitations are placed on the number of substituents, the alkyl group preferably has no greater than three substituents, and more preferably has one substituent.

The alkoxy group having a carbon number of at least 1 and no greater than 6 that is represented by $R_1$ to $R_{10}$ in the general formula (1) is preferably an alkoxy group having a carbon number of at least 1 and no greater than 3, and more preferably a methoxy group. The alkoxy group having a carbon number of at least 1 and no greater than 6 that is represented by $R_1$ to $R_{10}$ in the general formula (1) is optionally substituted. The alkoxy group having a carbon number of at least 1 and no greater than 6 may for example have, as a substituent, a halogen atom, an alkoxy group having a carbon number of at least 1 and no greater than 6, or an aryl group having a carbon number of at least 6 and no greater than 14. Although no particular limitations are placed on the number of substituents, the alkoxy group preferably has no greater than three substituents, and more preferably has one substituent.

The aryl group having a carbon number of at least 6 and no greater than 14 that is represented by $R_1$ to $R_{10}$ in the general formula (1) is preferably a monocyclic aromatic hydrocarbon group having a carbon number of at least 6 and no greater than 14, and more preferably a phenyl group. The aryl group having a carbon number of at least 6 and no greater than 14 that is represented by $R_1$ to $R_{10}$ in the general formula (1) is optionally substituted. The aryl group having a carbon number of at least 6 and no greater than 14 may for example have, as a substituent, a halogen atom, an alkyl group having a carbon number of at least 1 and no greater than 6, an alkoxy group having a carbon number of at least 1 and no greater than 6, or an aryl group having a carbon number of at least 6 and no greater than 14. Although no particular limitations are placed on the number of substituents, the aryl group preferably has no greater than three substituents, and more preferably has one substituent.

In the general formula (1), n represents an integer of at least 0 and no greater than 2. Preferably, n represents 1 or 2. As a result of n being 1 or 2, the benzidine derivative 1 has a moderately large molecular structure, and the distance (hopping distance) between the π electron cloud of a molecule of the benzidine derivative 1 and the π electron cloud of another adjacent molecule of the benzidine derivative 1 that are present in the photosensitive layer tends to be small. It is thought that as a result, hole mobility between molecules of the benzidine derivatives 1 is improved, and thus electrical properties of the photosensitive member is improved.

In order to improve electrical properties of the photosensitive member, $R_6$, $R_7$, $R_8$, $R_9$, and $R_{10}$ in the general formula (1) preferably each represent a hydrogen atom.

In order to inhibit crystallization in the photosensitive layer and improve electrical properties of the photosensitive member, $R_1$ to $R_{10}$ in the general formula (1) preferably each represent as follows. $R_1$, $R_2$, $R_3$, $R_4$, and $R_5$ each represent, independently of one another, a hydrogen atom, an alkyl group having a carbon number of at least 1 and no greater than 6 and optionally having an aryl group having a carbon number of at least 6 and no greater than 14, or an aryl group having a carbon number of at least 6 and no greater than 14. $R_6$, $R_7$, $R_8$, $R_9$, and $R_{10}$ each represent, independently of one another, a hydrogen atom or an alkoxy group having a carbon number of at least 1 and no greater than 6. n represents 0 or 1.

Specific examples of the benzidine derivative 1 include benzidine derivatives represented by chemical formulae (HT-1) to (HT-6) shown below. Hereinafter, the benzidine derivatives represented by the chemical formulae (HT-1) to (HT-6) may be referred to as benzidine derivatives HT-1 to HT-6.
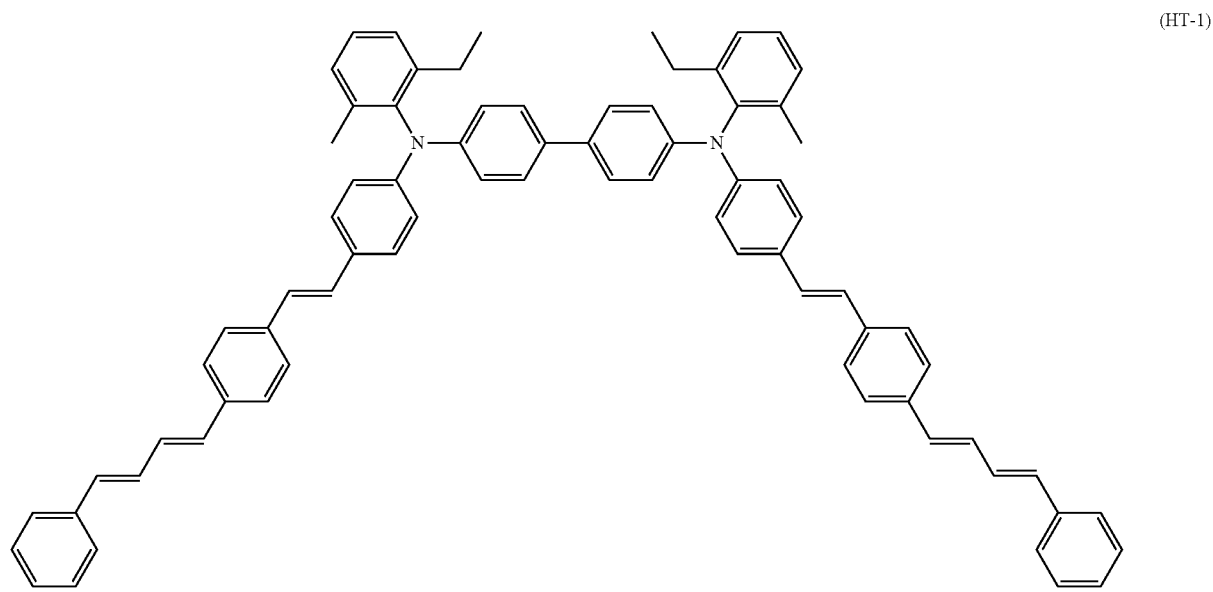
(HT-1)
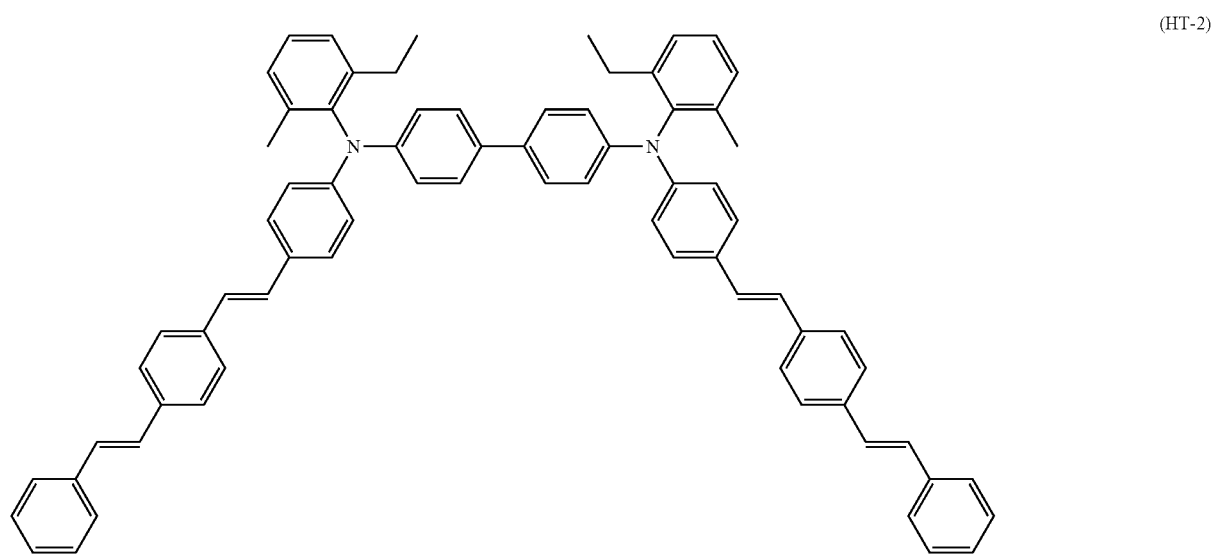
(HT-2)

-continued
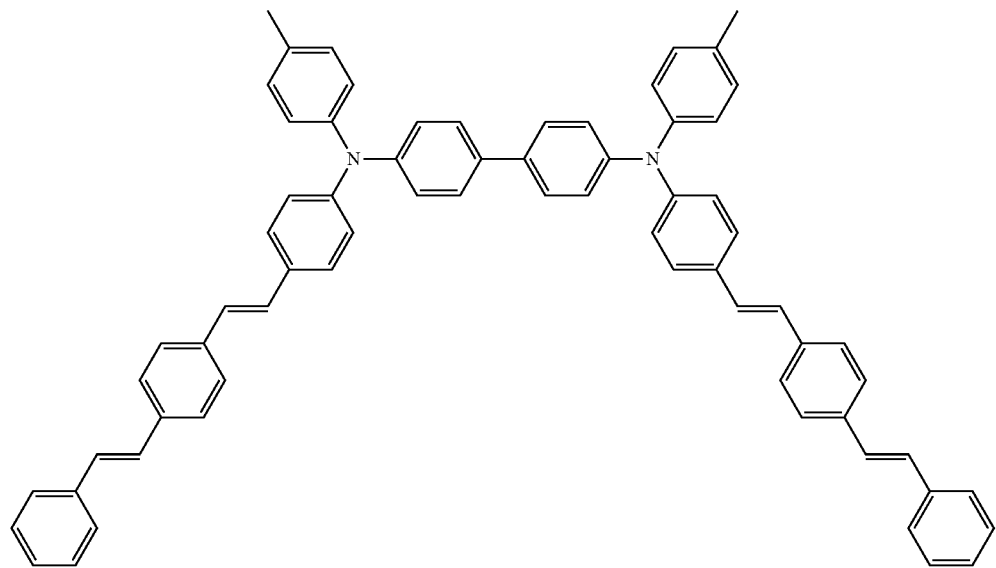
(HT-3)
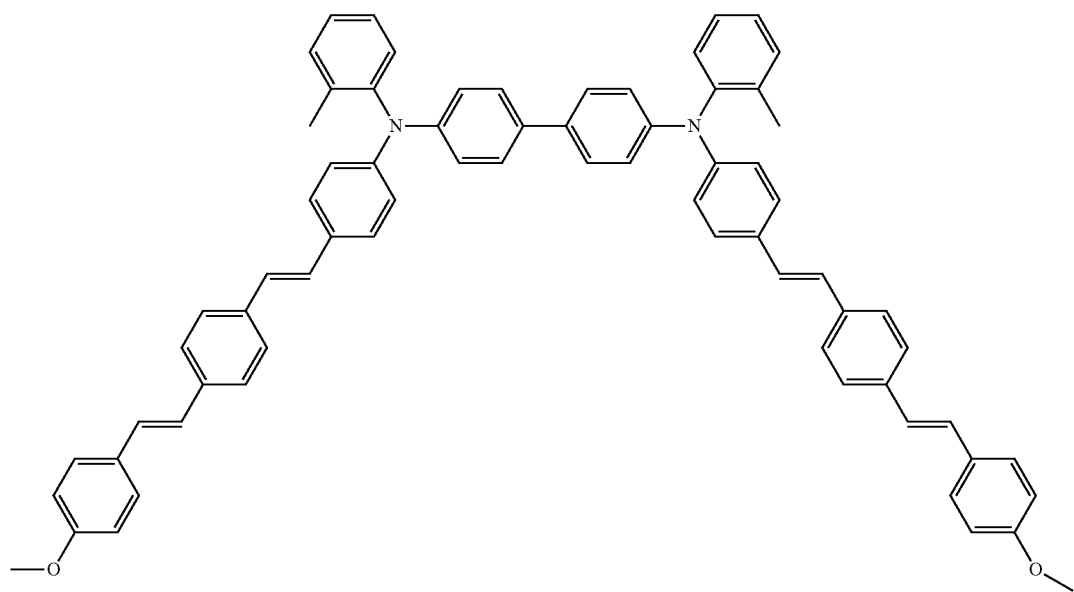
(HT-4)

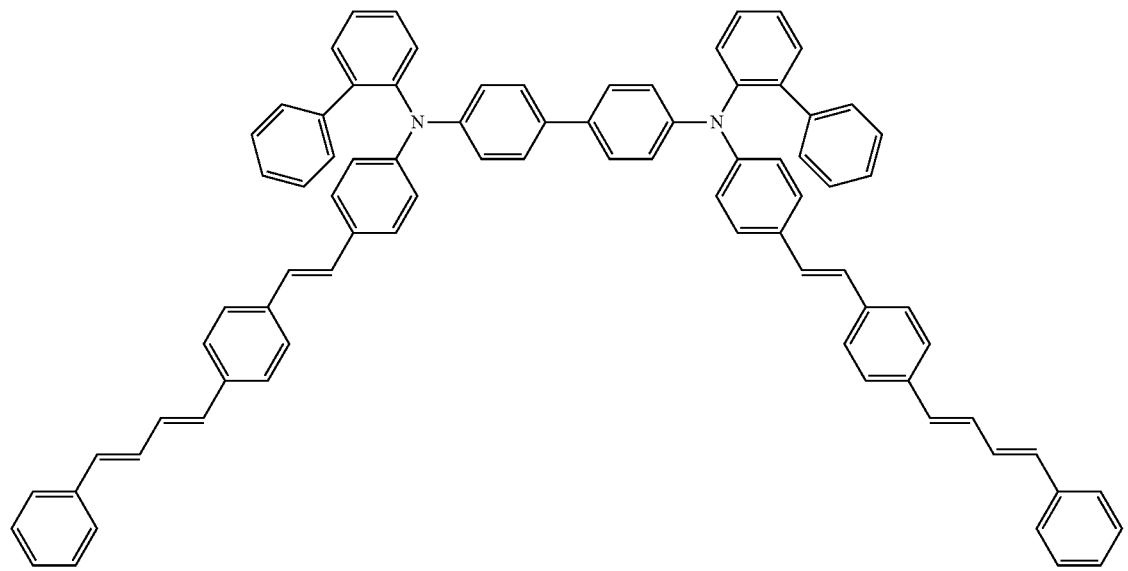
(HT-5)

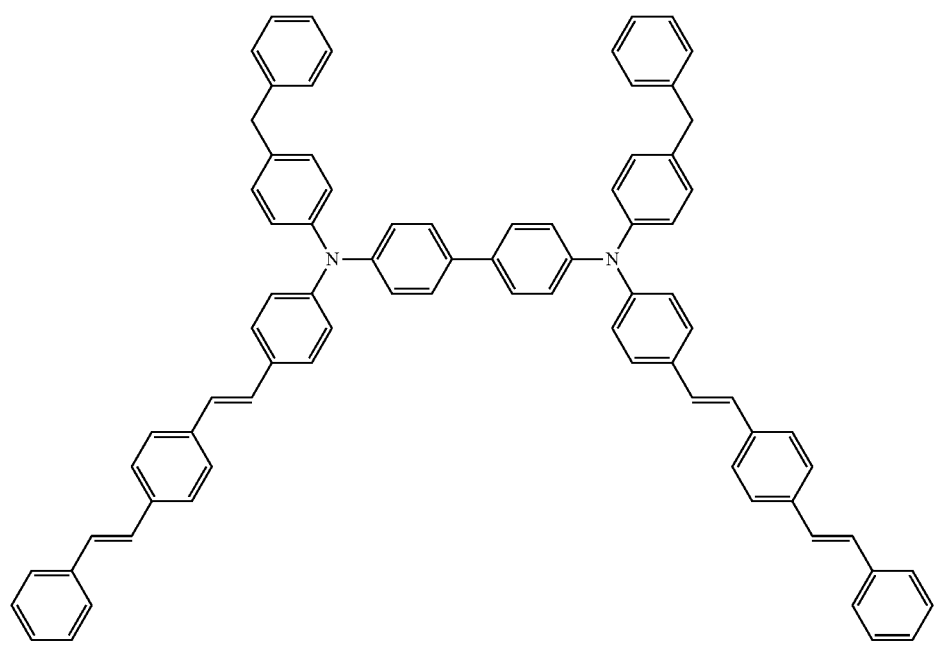
(HT-6)

[Method for Producing Benzidine Derivative]

Preferably, a method for producing the benzidine derivative 1 includes performing a reaction represented by scheme (R-6) shown below. Consequently, it is possible to readily produce the benzidine derivative 1 that inhibits crystallization in the photosensitive layer and improves electrical properties of the photosensitive member. The method for producing the benzidine derivative 1 may involve, as necessary, reactions represented by schemes (R-1) to (R-5) shown below. Where necessary, alterations can be made to the reactions as appropriate. Hereinafter, the reactions represented by the schemes (R-1) to (R-6) may be referred to as reactions R-1 to R-6.

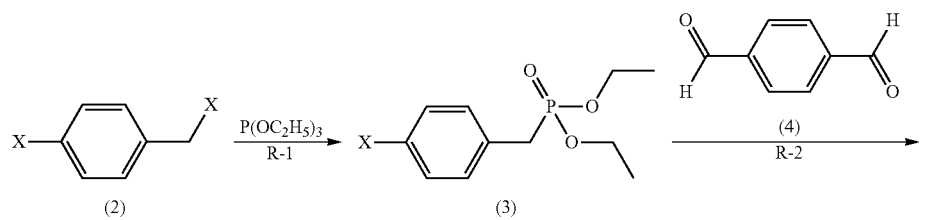
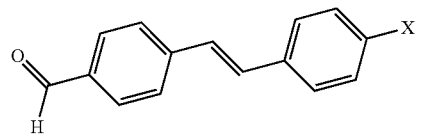
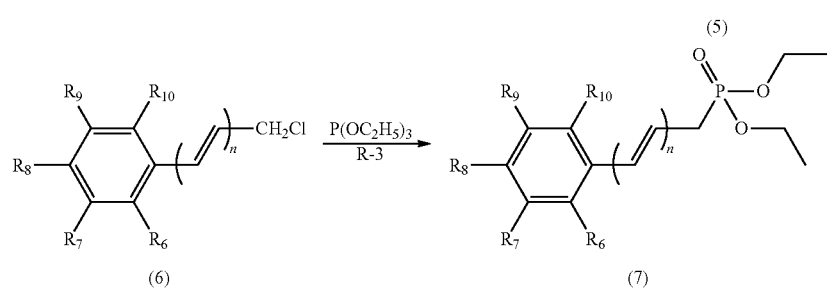
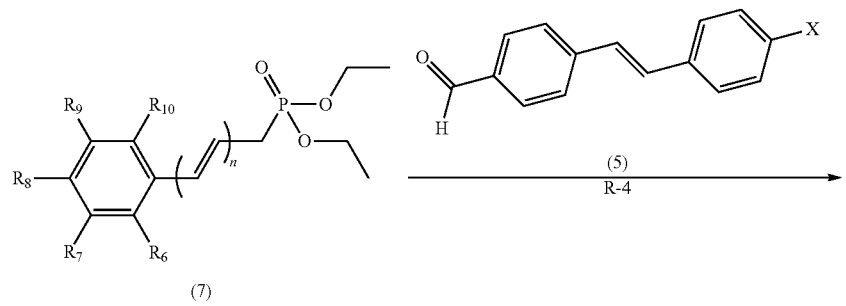
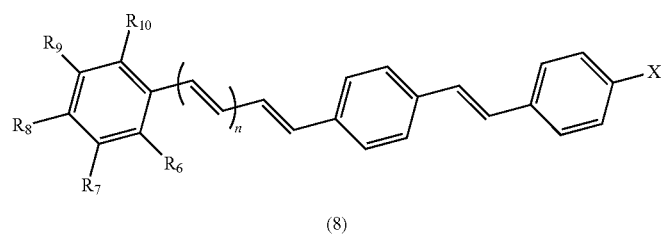
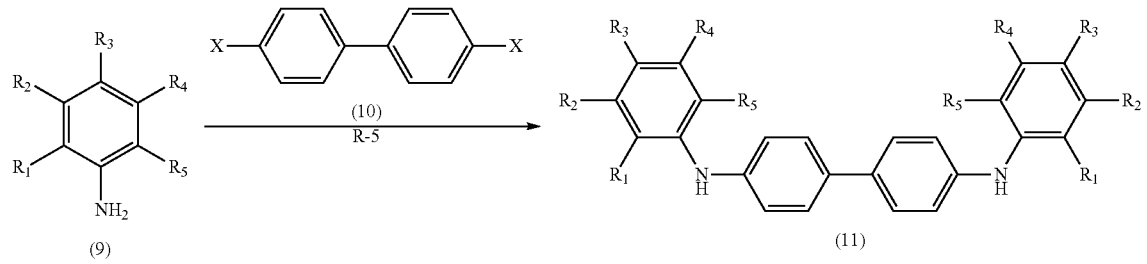

-continued

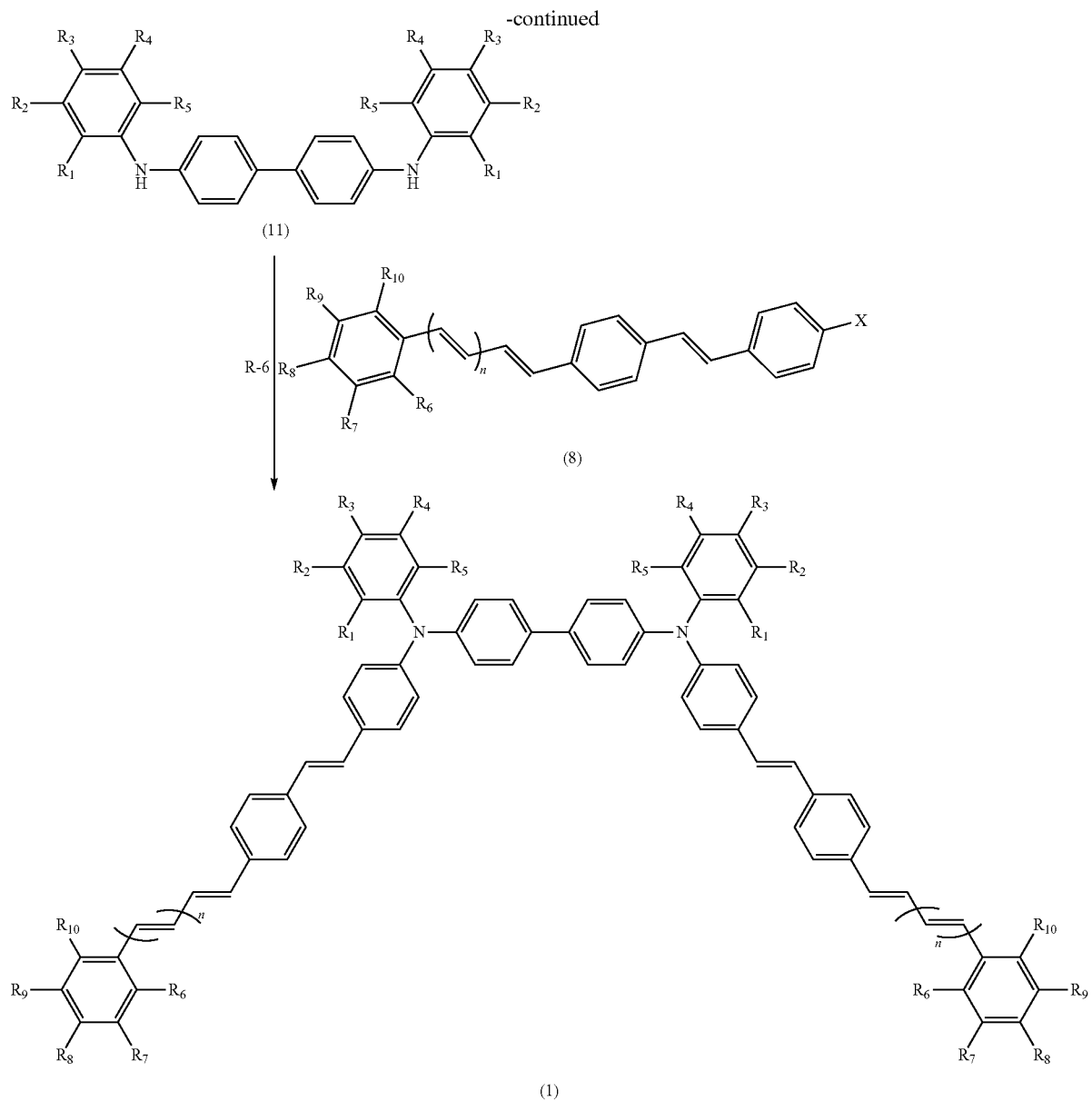

In the schemes (R-1) to (R-6), $R_1$, $R_2$, $R_3$, $R_4$, $R_5$, $R_6$, $R_7$, $R_8$, $R_9$, $R_{10}$, and n are the same as defined for $R_1$, $R_2$, $R_3$, $R_4$, $R_5$, $R_6$, $R_7$, $R_8$, $R_9$, $R_{10}$, and n in the general formula (1). X represents a halogen atom.

(Reaction R-1)

In the reaction R-1, the compound 2 (1 equivalent) is caused to react with triethyl phosphite (1 equivalent) to give the compound 3 (1 equivalent).

In the reaction R-1, at least one mole and no greater than 2.5 moles of triethyl phosphite is preferably added relative to 1 mole of the compound 2. If the number of moles of triethyl phosphite is too small relative to the number of moles of the compound 2, there may be a reduction in the yield of the compound 3. On the other hand, if the number of moles of the triethyl phosphite is too large relative to the number of moles of the compound 2, purification of the compound 3 after the reaction may be difficult due to triethyl phosphite remaining unreacted.

The reaction temperature of the reaction R-1 is preferably at least 160° C. and no greater than 200° C., and the reaction time thereof is preferably at least 2 hours and no greater than 10 hours.

(Reaction R-2)

In the reaction R-2, the compound 3 (1 equivalent) is caused to react with the compound 4 (1 equivalent) to give the compound 5 (1 equivalent). The reaction R-2 is a Wittig reaction.

In the reaction R-2, at least 1 mole and no greater than 10 moles of the compound 4 is preferably added relative to 1 mole of the compound 3. If the number of moles of the compound 4 is too small relative to the number of moles of the compound 3, there may be a reduction in the yield of the compound 5. If the number of moles of the compound 4 is too large relative to the number of moles of the compound 3, purification of the compound 5 may be difficult due to the compound 4 remaining unreacted.

The reaction R-2 may be carried out in the presence of a base. Examples of bases that can be used include sodium alkoxides (specifically, sodium methoxide and sodium ethoxide), metal hydrides (specifically, sodium hydride and potassium hydride), and metal salts (specifically, n-butyl lithium). Any one of the bases listed above may be used independently, or any two or more of the bases listed above may be used in combination. The additive amount of the base is preferably at least 1 mole and no greater than 2 moles relative to 1 mole of the compound 4. If the additive amount of the base is too small, there may be a reduction in reactivity. On the other hand, if the additive amount of the base is too large, the reaction may be difficult to control.

The reaction R-2 may be carried out in a solvent. Examples of solvents that can be used include ethers (specifically, tetrahydrofuran, diethyl ether, and dioxane), halogenated hydrocarbons (specifically, methylene chloride, chloroform, and dichloroethane), and aromatic hydrocarbons (specifically, benzene and toluene).

The reaction temperature of the reaction R-2 is preferably at least 0° C. and no greater than 50° C., and the reaction time thereof is preferably at least 2 hours and no greater than 24 hours.

(Reaction R-3)

In the reaction R-3, the compound 6 (1 equivalent) is caused to react with triethyl phosphite (1 equivalent) to give the compound 7 (1 equivalent).

In the reaction R-3, at least 1 mole and no greater than 2.5 moles of triethyl phosphite is preferably added relative to 1 mole of the compound 6. If the number of moles of triethyl phosphite is too small relative to the number of moles of the compound 6, there may be a reduction in the yield of the compound 7. On the other hand, if the number of moles of the triethyl phosphite is too large relative to the number of moles of the compound 6, purification of the compound 7 after the reaction may be difficult due to triethyl phosphite remaining unreacted.

The reaction temperature of the reaction R-3 is preferably at least 160° C. and no greater than 200° C., and the reaction time thereof is preferably at least 2 hours and no greater than 10 hours.

(Reaction R-4)

In the reaction R-4, the compound 7 (1 equivalent) is caused to react with the compound 5 (1 equivalent) to give the compound 8 (1 equivalent). The reaction R-4 is a Wittig reaction.

In the reaction R-4, at least 1 mole and no greater than 2.5 moles of the compound 5 is preferably added relative to 1 mole of the compound 7. If the number of moles of the compound 5 is too small relative to the number of moles of the compound 7, there may be a reduction in the yield of the compound 8. If the number of moles of the compound 5 is too large relative to the number of moles of the compound 7, purification of the compound 8 may be difficult due to the compound 5 remaining unreacted.

The reaction R-4 may be carried out in the presence of a base. Examples of bases that can be used are the same as for the reaction R-2. Any one of the bases listed above may be used independently, or any two or more of the bases listed above may be used in combination. The additive amount of the base is preferably at least 1 mole and no greater than 2 moles relative to 1 mole of the compound 5. If the additive amount of the base is too small, there may be a reduction in reactivity. On the other hand, if the additive amount of the base is too large, the reaction may be difficult to control.

The reaction R-4 may be carried out in a solvent. Examples of solvents that can be used are the same as for the reaction R-2. The reaction temperature of the reaction R-4 is preferably at least 0° C. and no greater than 50° C., and the reaction time thereof is preferably at least 2 hours and no greater than 24 hours.

(Reaction R-5)

In the reaction R-5, the compound 9 (2 equivalents) is caused to react with the compound 10 (1 equivalent) to give the compound 11 (1 equivalent). The reaction R-5 is a coupling reaction.

In the reaction R-5, at least 2 moles and no greater than 10 moles of the compound 9 is preferably added relative to 1 mole of the compound 10. If the number of moles of the compound 9 is too small relative to the number of moles of the compound 10, there may be a reduction in the yield of the compound 11. If the number of moles of the compound 9 is too large relative to the number of moles of the compound 10, purification of the compound 11 after the reaction may be difficult due to the compound 9 remaining unreacted.

The reaction temperature of the reaction R-5 is preferably at least 80° C. and no greater than 140° C., and the reaction time thereof is preferably at least 2 hours and no greater than 10 hours.

In the reaction R-5, a palladium compound is preferably used as a catalyst. Use of the palladium compound tends to enable a reduction in the activation energy of the reaction R-5. As a result, the yield of the compound 11 is expected to be increased. Examples of palladium compounds that can be used include tetravalent palladium compounds, divalent palladium compounds, and other palladium compounds. Specific examples of tetravalent palladium compounds include hexachloro palladium(IV) sodium tetrahydrate and hexachloro palladium(IV) potassium tetrahydrate. Specific examples of divalent palladium compounds include palladium(II) chloride, palladium(II) bromide, palladium(II) acetate, palladium(II) acetylacetate, dichlorobis(benzonitrile)palladium(II), dichlorobis(triphenylphosphine)palladium(II), dichlorotetramine palladium(II), and dichloro(cyclooctа-1,5-diene)palladium(II). Examples of other palladium compounds include tris(dibenzylideneacetone)dipalladium(0), tris(dibenzylideneacetone)dipalladium(0) chloroform complex, and tetrakis(triphenylphosphine)palladium(0). Any one of the palladium compounds listed above may be used independently, or any two or more of the palladium compounds listed above may be used in combination. The additive amount of the palladium compound is preferably at least 0.0005 moles and no greater than 20 moles relative to 1 mole of the compound 10, and more preferably at least 0.001 moles and no greater than 1 mole.

The palladium compound may have a structure including a ligand. As a result, reactivity of the reaction R-5 can be readily improved. Examples of ligands that can be used include tricyclohexylphosphine, triphenylphosphine, methyldiphenylphosphine, trifurylphosphine, tri(o-tolyl)phosphine, dicyclohexylphenylphosphine, tri(t-butyl)phosphine, 2,2'-bis(diphenylphosphino)-1,1'-binaphthyl, and 2,2'-bis[(diphenylphosphino)diphenyl] ether. Any one of the ligands listed above may be used independently, or any two or more of the ligands listed above may be used in combination. The additive amount of the ligand is preferably at least 0.0005 moles and no greater than 20 moles relative to 1 mole of the compound 10, and more preferably at least 0.001 moles and no greater than 1 mole.

The reaction R-5 is preferably carried out in the presence of a base. Through the presence of the base, hydrogen halide (for example, hydrogen chloride) produced in the reaction system can be quickly neutralized and catalytic activity can be improved. As a result, the yield of the compound 11 is expected to be improved. The base may be an inorganic base or an organic base. Preferably, organic bases for example include alkali metal alkoxides (specifically, sodium methoxide, sodium ethoxide, potassium methoxide, potassium ethoxide, lithium tert-butoxide, sodium tert-butoxide, and potassium tert-butoxide), with sodium tert-butoxide being more preferable. Examples of inorganic bases that can be used include tripotassium phosphate and cesium fluoride. In a situation in which at least 0.0005 moles and no greater than 20 moles of the palladium compound is added relative to 1 mole of the compound 10, the additive amount of the base is preferably at least 1 mole and no greater than 50 moles, and more preferably at least 1 mole and no greater than 30 moles.

The reaction R-5 may be carried out in a solvent. Examples of solvents that can be used include xylene (specifically, o-xylene), toluene, tetrahydrofuran, and dimethyl formamide.

(Reaction R-6)

In the reaction R-6, the compound 11(1 equivalent) is caused to react with the compound 8 (2 equivalents) to give the benzidine derivative 1 (1 equivalent). The reaction R-6 is a coupling reaction.

In the reaction R-6, at least 2 moles and no greater than 10 moles of the compound 8 is preferably added relative to 1 mole of the compound 11. If the number of moles of the compound 8 is too small relative to the number of moles of the compound 11, there may be a reduction in the yield of the benzidine derivative 1. On the other hand, if the number of moles of the compound 8 is too large relative to the number of moles of the compound 11, purification of the benzidine derivative 1 after the reaction may be difficult due to the compound 8 remaining unreacted.

The reaction temperature of the reaction R-6 is preferably at least 80° C. and no greater than 140° C., and the reaction time thereof is preferably at least 2 hours and no greater than 10 hours.

In the reaction R-6, a palladium compound is preferably used as a catalyst. Use of the palladium compound tends to enable a reduction in the activation energy of the reaction R-6. As a result, the yield of the benzidine derivative 1 is expected to be increased. Examples of palladium compounds that can be used are the same as for the reaction R-5. Any one of the palladium compounds listed above may be used independently, or any two or more of the palladium compounds listed above may be used in combination. The additive amount of the palladium compound is preferably at least 0.0005 moles and no greater than 20 moles relative to 1 mole of the compound 11, and more preferably at least 0.001 moles and no greater than 1 mole.

The palladium compound may have a structure including a ligand. As a result, reactivity of the reaction R-6 is expected to be improved. Examples of ligands that can be used are the same as for the reaction R-5. Any one of the ligands listed above may be used independently, or any two or more of the ligands listed above may be used in combination. The additive amount of the ligand is preferably at least 0.0005 moles and no greater than 20 moles relative to 1 mole of the compound 11, and more preferably at least 0.001 moles and no greater than 1 mole.

The reaction R-6 is preferably carried out in the presence of a base. Through the presence of the base, hydrogen halide (for example, hydrogen chloride) produced in the reaction system can be quickly neutralized and catalytic activity can be improved. As a result, the yield of the benzidine derivative 1 is expected to be increased. Examples of bases that can be used are the same as for the reaction R-5. In a situation in which at least 0.0005 moles and no greater than 20 moles of the palladium compound is added relative to 1 mole of the compound 11, the additive amount of the base is preferably at least 1 mole and no greater than 10 moles, and more preferably at least 1 mole and no greater than 5 moles.

The reaction R-6 may be carried out in a solvent. Examples of solvents that can be used are the same as for the reaction R-5.

Through the above, the benzidine derivative and the method for producing the benzidine derivative according to the present embodiment have been described. Through the benzidine derivative according to the present embodiment being contained in a photosensitive layer of a photosensitive member, crystallization in the photosensitive layer can be inhibited and electrical properties of the photosensitive member can be improved. The method for producing the triphenylamine derivative according to the present embodiment enables production of the benzidine derivative that inhibits crystallization in the photosensitive layer and improves electrical properties of the photosensitive member.

[Photosensitive Member]

The following describes a photosensitive member containing the benzidine derivative according to the present embodiment. The photosensitive member may be a multi-layer photosensitive member or a single-layer photosensitive member. The photosensitive member includes a photosensitive layer. The photosensitive layer contains at least a charge generating material and the benzidine derivative 1 as a hole transport material.

<1. Multi-Layer Photosensitive Member>

The following describes a configuration in which a photosensitive member 100 is a multi-layer photosensitive member with reference to FIGS. 3A to 3C. FIGS. 3A to 3C are schematic cross sectional views each illustrating a multi-layer photosensitive member, which is an example of the photosensitive member 100.

As illustrated in FIG. 3A, the multi-layer photosensitive member serving as the photosensitive member 100 includes a conductive substrate 20 and a photosensitive layer 30. The multi-layer photosensitive member includes, as the photosensitive layer 30, a charge generating layer 30a and a charge transport layer 30b. The conductive substrate 20 will be described later.

As illustrated in FIG. 3B, the charge transport layer 30b may be disposed on the conductive substrate 20 and the charge generating layer 30a may be disposed on the charge transport layer 30b in the multi-layer photosensitive member serving as the photosensitive member 100. However, the charge transport layer 30b typically has a greater film thickness than the charge generating layer 30a, and therefore the charge transport layer 30b is more resistant to damage than the charge generating layer 30a. In order to improve abrasion resistance of the multi-layer photosensitive member, therefore, the charge transport layer 30b is preferably disposed on the charge generating layer 30a as illustrated in FIG. 3A.

As illustrated in FIG. 3C, the multi-layer photosensitive member serving as the photosensitive member 100 may include the conductive substrate 20, the photosensitive layer 30, and an intermediate layer (undercoat layer) 40. The intermediate layer 40 is disposed between the conductive substrate 20 and the photosensitive layer 30. Furthermore, a protective layer (not illustrated) may be disposed on the photosensitive layer 30.

No particular limitations are placed on thicknesses of the charge generating layer 30a and the charge transport layer 30b so long as the thicknesses thereof are sufficient to enable the layers to implement their respective functions. The charge generating layer 30a preferably has a thickness of at least 0.01 82 m and no greater than 5 µm, and more preferably at least 0.1 µm and no greater than 3 µm. The charge transport layer 30b preferably has a thickness of at least 2 µm and no greater than 100 µm, and more preferably at least 5 µm and no greater than 50 µm.

The charge generating layer 30a in the photosensitive layer 30 contains a charge generating material. The charge generating layer 30a contains a charge generating layer binder resin (hereinafter, may be referred to as a base resin) and various additives as necessary. The charge generating material, the base resin, and the additives will be described later.

The charge transport layer 30b in the photosensitive layer 30 contains a hole transport material. The charge transport layer 30b may contain a binder resin, an electron acceptor compound, and various additives as necessary. The hole transport material, the binder resin, the electron acceptor compound, and the additives will be described later. Through the above, a configuration in which the photosensitive member 100 is a multi-layer photosensitive member has been described with reference to FIGS. 3A to 3C.

<2. Single-Layer Photosensitive Member>

The following describes a configuration in which the photosensitive member 100 is a single-layer photosensitive member with reference to FIGS. 4A to 4C. FIGS. 4A to 4C are schematic cross sectional views each illustrating a single-layer photosensitive member, which is another example of the photosensitive member 100.

As illustrated in FIG. 4A, the single-layer photosensitive member serving as the photosensitive member 100 includes the conductive substrate 20 and the photosensitive layer 30. The single-layer photosensitive member serving as the photosensitive member 100 includes a single-layer type photosensitive layer 30c as the photosensitive layer 30. The conductive substrate 20 will be described later.

As illustrated in FIG. 4B, the single-layer photosensitive member serving as the photosensitive member 100 may include the conductive substrate 20, the single-layer type photosensitive layer 30c, and the intermediate layer (undercoat layer) 40. The intermediate layer 40 is disposed between the conductive substrate 20 and the single-layer type photosensitive layer 30c. Furthermore, as illustrated in FIG. 4C, a protective layer 50 may be disposed on the single-layer type photosensitive layer 30c.

No particular limitations are placed on thickness of the single-layer type photosensitive layer 30c, so long as the thickness thereof is sufficient to enable the single-layer type photosensitive layer 30c to function as a single-layer type photosensitive layer. The single-layer type photosensitive layer 30c preferably has a thickness of at least 5 µm and no greater than 100 µm, and more preferably at least 10 µm and no greater than 50 µm.

The single-layer type photosensitive layer 30c serving as the photosensitive layer 30 contains a charge generating material and a hole transport material. The single-layer type photosensitive layer 30c may contain an electron transport material, a binder resin, and various additives as necessary. The hole transport material, the charge generating material, the electron transport material, the binder resin, and the additives will be described later. Through the above, a configuration in which the photosensitive member 100 is a single-layer photosensitive member has been described with reference to FIGS. 4A to 4C.

The following describes elements of configuration that are common to the photosensitive member for both the multi-layer photosensitive member and the single-layer photosensitive member.

<3. Conductive Substrate>

No particular limitations are placed on the conductive substrate other than being a conductive substrate that can be used in photosensitive members. At least a surface portion of the conductive substrate is formed from a conductive material. An example of the conductive substrate is a conductive substrate formed from a conductive material. Another example of the conductive substrate is a conductive substrate formed through coating with a conductive material. Examples of conductive materials that can be used include aluminum, iron, copper, tin, platinum, silver, vanadium, molybdenum, chromium, cadmium, titanium, nickel, palladium, indium, stainless steel, and brass. Any one of the conductive materials listed above may be used independently, or any two or more of the conductive materials listed above may be used in combination (for example, as an alloy). Of the conductive materials listed above, aluminum or aluminum alloy is preferable in terms of good charge mobility from the photosensitive layer to the conductive substrate.

The shape of the conductive substrate is selected as appropriate in accordance with the structure of an image forming apparatus in which the conductive substrate is to be used. The conductive substrate may for example be sheet-shaped or drum-shaped. Furthermore, the thickness of the conductive substrate is selected as appropriate in accordance with the shape of the conductive substrate.

<4. Hole Transport Material>

The photosensitive layer contains the benzidine derivative 1 as a hole transport material. In a configuration in which the photosensitive member is a multi-layer photosensitive member, the charge transport layer contains the benzidine derivative 1 as the hole transport material. In a configuration in which the photosensitive member is a single-layer photosensitive member, the single-layer type photosensitive layer contains the benzidine derivative 1 as the hole transport material. As a result of the photosensitive layer containing the benzidine derivative 1, as already described above, crystallization in the photosensitive layer can be inhibited and electrical properties of the photosensitive member can be improved.

<5. Charge Generating Material>

In a configuration in which the photosensitive member is a multi-layer photosensitive member, the charge generating layer contains a charge generating material. In a configuration in which the photosensitive member is a single-layer photosensitive member, the single-layer type photosensitive layer contains a charge generating material.

No particular limitations are placed on the charge generating material other than being a charge generating material that can be used in photosensitive members. Examples of charge generating materials that can be used include phthalocyanine-based pigments, perylene-based pigments, bisazo pigments, trisazo pigments, dithioketopyrrolopyrrole pigments, metal-free naphthalocyanine pigments, metal naphthalocyanine pigments, squaraine pigments, indigo pigments, azulenium pigments, cyanine pigments, powders of inorganic photoconductive materials (for example, selenium, selenium-tellurium, selenium-arsenic, cadmium sulfide, or amorphous silicon), pyrylium pigments, anthanthrone-based pigments, triphenylmethane-based pigments, threne-based pigments, toluidine-based pigments, pyrazoline-based pigments, and quinacridone-based pigments.

Examples of phthalocyanine-based pigments that can be used include a metal-free phthalocyanine represented by chemical formula (CG-1) and metal phthalocyanine. Examples of the metal phthalocyanine include titanyl phthalocyanine represented by chemical formula (CG-2), hydroxygallium phthalocyanine, and chlorogallium phthalocyanine. The phthalocyanine-based pigment may be crystalline or non-crystalline. No particular limitations are placed on the crystal structure (for example, α-form, β-form, Y-form, V-form, or II-form) of the phthalocyanine-based pigment, and phthalocyanine-based pigments having various different crystal structures may be used.

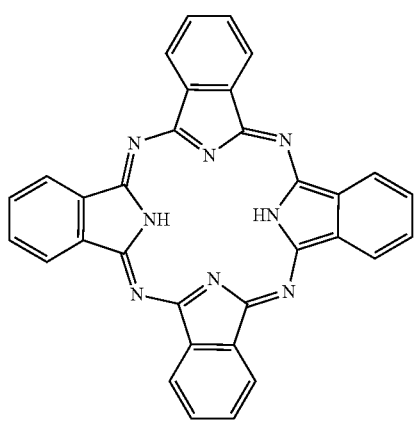

(CG-1)

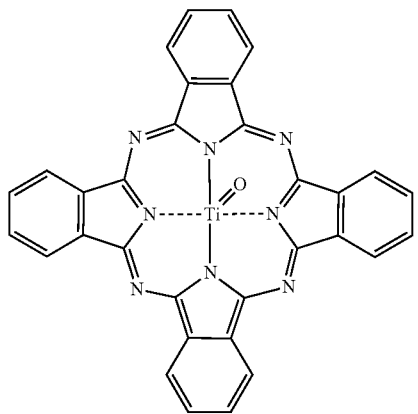

(CG-2)

Examples of crystalline metal-free phthalocyanine that can be used include metal-free phthalocyanine having an X-form crystal structure (hereinafter, may be referred to as X-form metal-free phthalocyanine). Examples of crystalline titanyl phthalocyanine include titanyl phthalocyanine having an α-form, β-form, or Y-form crystal structure (hereinafter, may be referred to as α-form, β-form, or Y-form titanyl phthalocyanine). Examples of crystalline hydroxygallium phthalocyanine include hydroxygallium phthalocyanine having a V-form crystal structure. Examples of crystalline chlorogallium phthalocyanine include chlorogallium phthalocyanine having a II-form crystal structure. X-form metal-free phthalocyanine and Y-form titanyl phthalocyanine are preferable as each having a high quantum yield for a wavelength region of 700 nm or greater. In order to particularly improve electrical properties in the case of the photosensitive layer containing the benzidine derivative 1 as the hole transport material, Y-form titanyl phthalocyanine is more preferable.

Y-form titanyl phthalocyanine for example exhibits a major peak at a Bragg angle (2θ±0.2°) of 27.2° with respect to CuKα characteristic X-ray diffraction spectrum. The term major peak refers to a most intense or second most intense peak within a range of Bragg angles (2θ±0.2°) from 3° to 40° in a CuKα characteristic X-ray diffraction spectrum.

(Method for Measuring CuKα Characteristic X-Ray Diffraction Spectrum)

An example of methods for measuring a CuKα characteristic X-ray diffraction spectrum will be described. A sample (titanyl phthalocyanine) is loaded into a sample holder of an X-ray diffraction spectrometer (for example, "RINT (registered Japanese trademark) 1100", product of Rigaku Corporation) and an X-ray diffraction spectrum is measured using a Cu X-ray tube, a tube voltage of 40 kV, a tube current of 30 mA, and X-rays characteristic of CuKα having a wavelength of 1.542 Å. The measurement range (2θ) is for example from 3° to 40° (start angle: 3°, stop angle: 40°) and the scanning speed is for example 10°/minute.

A single charge generating material having an absorption wavelength in a desired region or a combination of two or more charge generating materials may be used. Also, for example in a digital optical system image forming apparatus (for example, a laser beam printer or facsimile machine in which a light source such as a semiconductor laser is used), a photosensitive member that is sensitive to a range of wavelengths that are greater than or equal to 700 nm is preferably used. Accordingly, for example, a phthalocyanine-based pigment is preferable, metal-free phthalocyanine or titanyl phthalocyanine is more preferable, and X-form metal-free phthalocyanine or Y-form titanyl phthalocyanine is particularly preferable. One charge generating material may be used independently, or two or more charge generating materials may be used in combination.

For a photosensitive member applied to an image forming apparatus that uses a short-wavelength laser light source (for example, a laser light source having an approximate wavelength of at least 350 nm and no greater than 550 nm), an anthanthrone-based pigment is preferably used as the charge generating material.

In a configuration in which the photosensitive member is a multi-layer photosensitive member, the amount of the charge generating material is preferably at least 5 parts by mass and no greater than 1,000 parts by mass relative to 100 parts by mass of the base resin contained in the charge generating layer, and more preferably at least 30 parts by mass and no greater than 500 parts by mass.

In a configuration in which the photosensitive member is a single-layer photosensitive member, the amount of the charge generating material is preferably at least 0.1 parts by mass and no greater than 50 parts by mass relative to 100 parts by mass of the binder resin contained in the single-layer type photosensitive layer, and more preferably at least 0.5 parts by mass and no greater than 30 parts by mass.

<6. Electron Transport Material and Electron Acceptor Compound>

In a configuration in which the photosensitive member is a multi-layer photosensitive member, the charge transport layer may contain an electron acceptor compound as necessary. As a result, the hole transport by the hole transport material tends to be improved. On the other hand, in a situation in which the photosensitive member is a single-layer photosensitive member, the single-layer type photosensitive layer may contain an electron transport material as necessary. Through inclusion of the electron transport material, the single-layer type photosensitive layer can transport electrons and the single-layer type photosensitive layer can be easily provided with bipolar properties.

Examples of electron transport materials or electron acceptor compounds that can be used include quinone-based compounds, diimide-based compounds, hydrazone-based compounds, malononitrile-based compounds, thiopyran-based compounds, trinitrothioxanthone-based compounds, 3,4,5,7-tetranitro-9-fluorenone-based compounds, dinitroanthracene-based compounds, dinitroacridine-based compounds, tetracyanoethylene, 2,4,8-trinitrothioxanthone, dinitrobenzene, dinitroacridine, succinic anhydride, maleic anhydride, and dibromomaleic anhydride. Examples of quinone-based compounds that can be used include diphenoquinone-based compounds, azoquinone-based compounds, anthraquinone-based compounds, naphthoquinone-based compounds, nitroanthraquinone-based compounds, and dinitroanthraquinone-based compounds. One electron transport material may be used independently, or two or more electron transport materials may be used in combination. Likewise, one electron acceptor compound may be used independently, or two or more electron acceptor compounds may be used in combination.

Examples of the electron transport material or the electron acceptor include compounds represented by general formulae (12) to (14).

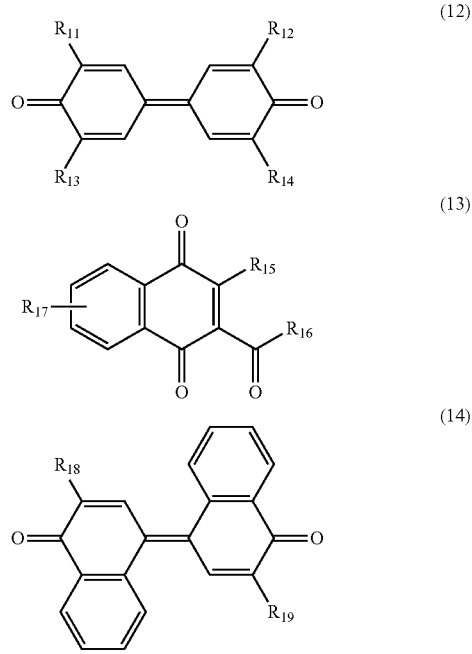

In the general formulae (12) to (14), $R_{11}$ to $R_{19}$ each represent, independently of one another, a hydrogen atom, a cyano group, an optionally substituted alkyl group, an optionally substituted alkenyl group, an optionally substituted alkoxy group, an optionally substituted alkoxycarbonyl group, an optionally substituted aryl group, or an optionally substituted heterocyclic group.

The alkyl group represented by $R_{11}$ to $R_{19}$ in the general formulae (12) to (14) is for example an alkyl group having a carbon number of at least 1 and no greater than 6. The alkyl group having a carbon number of at least 1 and no greater than 6 is preferably an alkyl group having a carbon number of at least 1 and no greater than 5, and more preferably a methyl group, a 1,1-dimethylpropyl group, or a tert-butyl group. The alkyl group is optionally substituted. The alkyl group may for example have, as a substituent, a halogen atom, a hydroxyl group, an alkoxy group having a carbon number of at least 1 and no greater than 6, an aryl group having a carbon number of at least 6 and no greater than 14 and optionally bearing further substituents, or a cyano group. Although no particular limitations are placed on the number of substituents, the alkyl group preferably has no greater than three substituents. Examples of substituents that are further borne by the aryl group that is a substituent of alkyl and that has a carbon number of at least 6 and no greater than 14 include a halogen atom, a hydroxyl group, an alkyl group having a carbon number of at least 1 and no greater than 6, an alkoxy group having a carbon number of at least 1 and no greater than 6, a nitro group, a cyano group, an alkanoyl group having a carbon number of at least 2 and no greater than 7 (a group formed through bonding of a carbonyl group with an alkyl group having a carbon number of at least 1 and no greater than 6), a benzoyl group, a phenoxy group, an alkoxycarbonyl group having a carbon number of at least 2 and no greater than 7 (a group formed through bonding of a carbonyl group with an alkoxy group having a carbon number of at least 1 and no greater than 6), and a phenoxycarbonyl group.

The alkenyl group represented by $R_{11}$ to $R_{19}$ in the general formulae (12) to (14) is for example an unsubstituted straight chain or branched chain alkenyl group having a carbon number of at least 2 and no greater than 6. The alkenyl group having a carbon number of at least 2 and no greater than 6 for example has at least one and no greater than three double bonds. The alkenyl group having a carbon number of at least 2 and no greater than 6 is for example a vinyl group, a propenyl group, a butenyl group, a pentenyl group, a pentadienyl group, a hexenyl group, or a hexadienyl group. The alkenyl group is optionally substituted. The alkenyl group may for example have, as a substituent, a halogen atom, a hydroxyl group, an alkoxy group having a carbon number of at least 1 and no greater than 6, an aryl group having a carbon number of at least 6 and no greater than 14, or a cyano group. Although no particular limitations are placed on the number of substituents, the alkenyl group preferably has no greater than three substituents.

The alkoxy group represented by $R_{11}$ to $R_{19}$ in the general formulae (12) to (14) is for example an alkoxy group having a carbon number of at least 1 and no greater than 6. The alkoxy group having a carbon number of at least 1 and no greater than 6 is preferably an alkoxy group having a carbon number of at least 1 and no greater than 3, and more preferably a methoxy group. The alkoxy group is optionally substituted. The alkoxy group may for example have, as a substituent, a halogen atom, a hydroxyl group, an alkoxy group having a carbon number of at least 1 and no greater than 6, an aryl group having a carbon number of at least 6 and no greater than 14, or a cyano group. Preferably, the substituent is a phenyl group. Although no particular limitations are placed on the number of substituents, the alkoxy group preferably has no greater than three substituents, and more preferably has one substituent.

The alkoxycarbonyl group represented by $R_{11}$ to $R_{19}$ in the general formulae (12) to (14) is for example an alkoxycarbonyl group having a carbon number of at least 2 and no greater than 7. An alkoxycarbonyl group having a carbon number of at least 2 and no greater than 7 as used herein refers to a group formed through bonding of a carbonyl group with an unsubstituted straight chain or branched chain alkoxy group having a carbon number of at least 1 and no greater than 6. The alkoxycarbonyl group is optionally substituted. The alkoxycarbonyl group may for example have, as a substituent, a halogen atom, a hydroxyl group, an alkoxy group having a carbon number of at least 1 and no greater than 6, an aryl group having a carbon number of at least 6 and no greater than 14, or a cyano group. Although no particular limitations are placed on the number of substituents, the alkoxycarbonyl group preferably has no greater than three substituents.

The aryl group represented by $R_{11}$ to $R_{19}$ in the general formulae (12) to (14) is for example an aryl group having a carbon number of at least 6 and no greater than 14. The aryl group having a carbon number of at least 6 and no greater than 14 is preferably a phenyl group. The aryl group is optionally substituted. The aryl group may for example have, as a substituent, a halogen atom, a hydroxyl group, an alkyl group having a carbon number of at least 1 and no greater than 6, an alkoxy group having a carbon number of at least 1 and no greater than 6, a nitro group, a cyano group, an alkanoyl group having a carbon number of at least 2 and no greater than 7 (a group formed through bonding of a carbonyl group with an alkyl group having a carbon number of at least 1 and no greater than 6), a benzoyl group, a phenoxy group, an alkoxycarbonyl group having a carbon number of at least 2 and no greater than 7 (a group formed through bonding of a carbonyl group with an alkoxy group having a carbon number of at least 1 and no greater than 6), a phenoxycarbonyl group, an aryl group having a carbon number of at least 6 and no greater than 14, or a biphenyl group. Although no particular limitations are placed on the number of substituents, the aryl group preferably has no greater than three substituents.

The heterocyclic group represented by $R_{11}$ to $R_{19}$ in the general formulae (12) to (14) is for example a heterocyclic group formed by a five- or six-membered monocyclic ring including at least one hetero atom selected from the group consisting of N, S, and O; a heterocyclic group resulting from condensation of a plurality of such monocyclic rings; or a heterocyclic group resulting from condensation of such a monocyclic ring with a five- or six-membered hydrocarbon ring. In a configuration in which the heterocyclic group is a fused ring structure, the fused ring structure preferably includes no greater than three rings. The heterocyclic group may for example have, as a substituent, a halogen atom, a hydroxyl group, an alkyl group having a carbon number of at least 1 and no greater than 6, an alkoxy group having a carbon number of at least 1 and no greater than 6, a nitro group, a cyano group, an alkanoyl group having a carbon number of at least 2 and no greater than 7 (a group formed through bonding of a carbonyl group with an alkyl group having a carbon number of at least 1 and no greater than 6), a benzoyl group, a phenoxy group, an alkoxycarbonyl group having a carbon number of at least 2 and no greater than 7 (a group formed through bonding of a carbonyl group with an alkoxy group having a carbon number of at least 1 and no greater than 6), and a phenoxycarbonyl group. Although no particular limitations are placed on the number of substituents, the heterocyclic group preferably has no greater than three substituents.

In order to improve electrical properties of the photosensitive member in which the photosensitive layer is a single-layer type photosensitive layer and that contains the benzidine derivative 1 as a hole transport material, the compound represented by the general formula (12) is preferably used.

Specific examples of the compounds represented by the general formulae (12) to (14) include compounds represented by chemical formulae (ET-1) to (ET-3). Hereinafter, the compounds represented by the chemical formulae (ET-1) to (ET-3) may be referred to as compounds ET-1 to ET-3.

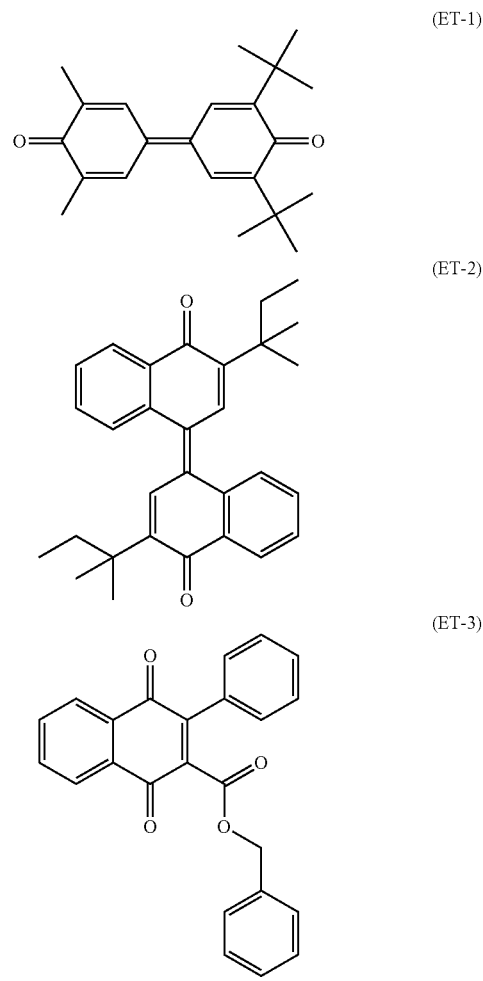

In a configuration in which the photosensitive member is a multi-layer photosensitive member, the amount of the electron acceptor compound is preferably at least 0.1 parts by mass and no greater than 20 parts by mass relative to 100 parts by mass of the binder resin contained in the charge transport layer, and more preferably at least 0.5 parts by mass and no greater than 10 parts by mass.

In a configuration in which the photosensitive member is a single-layer photosensitive member, the amount of the electron transport material is preferably at least 5 parts by mass and no greater than 100 parts by mass relative to 100 parts by mass of the binder resin contained in the single-layer type photosensitive layer, and more preferably at least 10 parts by mass and no greater than 80 parts by mass.

<7. Binder Resin>

In a configuration in which the photosensitive member is a multi-layer photosensitive member, the charge transport layer contains a binder resin. In a configuration in which the photosensitive member is a single-layer photosensitive member, the single-layer type photosensitive layer contains a binder resin.

Examples of binder resins that can be used include thermoplastic resins, thermosetting resins, and photocurable resins. Examples of thermoplastic resins that can be used include polycarbonate resins, polyarylate resins, styrene-butadiene copolymers, styrene-acrylonitrile copolymers, styrene-maleic acid copolymers, acrylic acid copolymers, styrene-acrylic acid copolymers, polyethylene resins, ethylene-vinyl acetate copolymers, chlorinated polyethylene resins, polyvinyl chloride resins, polypropylene resins, ionomer resins, vinyl chloride-vinyl acetate copolymers, alkyd resins, polyamide resins, urethane resins, polysulfone resins, diallyl phthalate resins, ketone resins, polyvinyl butyral resins, polyester resins, and polyether resins. Examples of thermosetting resins that can be used include silicone resins, epoxy resins, phenolic resins, urea resins, and melamine resins. Examples of photocurable resins that can be used include epoxy acrylate (acrylic acid adducts of epoxy compounds) and urethane acrylate (acrylic acid adducts of urethane compounds). Any one of the binder resins listed above may be used independently, or any two or more of the binder resins listed above may be used in combination.

Of the binder resins listed above, polycarbonate resins are preferable for obtaining a single-layer type photosensitive layer and a charge transport layer having excellent balance in terms of processability, mechanical properties, optical properties, and abrasion resistance. Examples of polycarbonate resins that can be used include bisphenol Z polycarbonate resin, bisphenol ZC polycarbonate resin, bisphenol C polycarbonate resin, and bisphenol A polycarbonate resin.

The binder resin preferably has a viscosity average molecular weight of at least 40,000, and more preferably at least 40,000 and no greater than 52,500. As a result of the binder resin having a viscosity average molecular weight of at least 40,000, abrasion resistance of the photosensitive member can be readily improved. As a result of the binder resin having a viscosity average molecular weight of no greater than 52,500, the binder resin has a high tendency to dissolve in a solvent and viscosity of an application liquid for charge transport layer formation or an application liquid for single-layer type photosensitive layer formation has a low tendency to be too high during photosensitive layer formation. Consequently, the charge transport layer or the single-layer type photosensitive layer can be readily formed.

<8. Base Resin>

In a configuration in which the photosensitive member is a multi-layer photosensitive member, the charge generating layer contains a base resin. No particular limitations are placed on the base resin so long as the base resin can be used in photosensitive members. Examples of base resins that can be used include thermoplastic resins, thermosetting resins, and photocurable resins. Examples of thermoplastic resins that can be used include styrene-butadiene copolymers, styrene-acrylonitrile copolymers, styrene-maleic acid copolymers, styrene-acrylic acid copolymers, acrylic copolymers, polyethylene resins, ethylene-vinyl acetate copolymers, chlorinated polyethylene resins, polyvinyl chloride resins, polypropylene resins, ionomers, vinyl chloride-vinyl acetate copolymers, alkyd resins, polyamide resins, urethane resins, polycarbonate resins, polyarylate resins, polysulfone resins, diallyl phthalate resins, ketone resins, polyvinyl butyral resins, polyether resins, and polyester resins. Examples of thermosetting resins that can be used include silicone resins, epoxy resins, phenolic resins, urea resins, melamine resins, and other crosslinkable thermosetting resins. Examples of photocurable resins that can be used include epoxy acrylate (acrylic acid adducts of epoxy compounds) and urethane acrylate (acrylic acid adducts of urethane compounds). Any one of the base resins listed above may be used independently, or any two or more of the base resins listed above may be used in combination.

Preferably, the base resin contained in the charge generating layer is different from the binder resin contained in the charge transport layer for the following reason. In production of a multi-layer photosensitive member, for example, a charge generating layer is formed on a conductive substrate, and a charge transport layer is formed on the charge generating layer. In the formation of the charge transport layer, an application liquid for charge transport layer formation is applied onto the charge generating layer. Therefore, the charge generating layer is preferably insoluble in a solvent of the application liquid for charge transport layer formation.

<9. Additive>

The photosensitive layer of the photosensitive member (the charge generating layer, the charge transport layer, or the single-layer type photosensitive layer) may contain various additives as necessary. Examples of additives that can be used include antidegradants (specific examples include antioxidants, radical scavengers, singlet quenchers, and ultraviolet absorbing agents), softeners, surface modifiers, extending agents, thickeners, dispersion stabilizers, waxes, acceptors, donors, surfactants, plasticizers, sensitizers, and leveling agents. Examples of antioxidants include hindered phenols (specific examples include di(tert-butyl)p-cresol), hindered amines, paraphenylenediamine, arylalkanes, hydroquinone, spirochromanes, spiroindanones, derivatives of any of the above compounds, organosulfur compounds, and organophosphorus compounds.

<10. Intermediate Layer>

The intermediate layer (undercoat layer) for example contains inorganic particles and a resin for intermediate layer use (intermediate layer resin). Provision of the intermediate layer may facilitate flow of current generated when the photosensitive member is exposed to light and inhibit increasing resistance, while also maintaining insulation to a sufficient degree so as to inhibit leakage current from occurring.

Examples of inorganic particles that can be used include particles of metals (for example, aluminum, iron, and copper), particles of metal oxides (for example, titanium oxide, alumina, zirconium oxide, tin oxide, and zinc oxide), and particles of non-metal oxides (for example, silica). Any one type of the inorganic particles listed above may be used independently, or any two or more types of the inorganic particles listed above may be used in combination.

No particular limitations are placed on the intermediate layer resin so long as the resin can be used for forming the intermediate layer. The intermediate layer may contain various additives. The additives are the same as defined for the additives for the photosensitive layer.

<11. Method for Producing Photosensitive Member>

In a configuration in which the photosensitive member is a multi-layer photosensitive member, the multi-layer photosensitive member is for example produced as described below. First, an application liquid for charge generating layer formation and an application liquid for charge transport layer formation are prepared. The application liquid for charge generating layer formation is applied onto the conductive substrate and dried to form the charge generating layer. Next, the application liquid for charge transport layer formation is applied onto the charge generating layer and dried to form the charge transport layer. Through the above, the multi-layer photosensitive member is produced.

The application liquid for charge generating layer formation is prepared by dissolving or dispersing a charge generating material and optional components (for example, a base resin and various additives), depending on necessity thereof, in a solvent. The application liquid for charge transport layer formation is prepared by dissolving or dispersing a hole transport material and optional components (for example, a binder resin, an electron acceptor compound, and various additives), depending on necessity thereof, in a solvent.

In a configuration in which the photosensitive member is a single-layer photosensitive member, the single-layer photosensitive member is for example produced as described below. The single-layer photosensitive member is produced by applying an application liquid for single-layer type photosensitive layer formation onto the conductive substrate and drying the application liquid for single-layer type photosensitive layer formation. The application liquid for single-layer type photosensitive layer formation is prepared by dissolving or dispersing a charge generating material, a hole transport material, and optional components (for example, an electron transport material, a binder resin, and various additives), depending on necessity thereof, in a solvent.

No particular limitations are placed on the solvents contained in the application liquids (the application liquid for charge generating layer formation, the application liquid for charge transport layer formation, or the application liquid for single-layer type photosensitive layer formation) other than that the components of each of the application liquids should be soluble or dispersible in the solvent. Examples of solvents that can be used include alcohols (specific examples include methanol, ethanol, isopropanol, and butanol), aliphatic hydrocarbons (specific examples include n-hexane, octane, and cyclohexane), aromatic hydrocarbons (specific examples include benzene, toluene, and xylene), halogenated hydrocarbons (specific examples include dichloromethane, dichloroethane, carbon tetrachloride, and chlorobenzene), ethers (specific examples include dimethyl ether, diethyl ether, tetrahydrofuran, ethylene glycol dimethyl ether, diethylene glycol dimethyl ether, and propylene glycol monomethyl ether), ketones (specific examples include acetone, methyl ethyl ketone, and cyclohexanone), esters (specific examples include ethyl acetate and methyl acetate), dimethyl formaldehyde, dimethyl formamide, and dimethyl sulfoxide. Any one of the solvents listed above may be used independently, or any two or more of the solvents listed above may be used in combination. In order to improve workability in production of the photosensitive member, a non-halogenated solvent (a solvent other than a halogenated hydrocarbon) is preferably used.

Each of the application liquids is prepared by mixing the components in order to disperse the components in the solvent. Mixing or dispersion can for example be performed using a bead mill, a roll mill, a ball mill, an attritor, a paint shaker, or an ultrasonic disperser.

Each of the application liquids (the application liquid for charge generating layer formation, the application liquid for charge transport layer formation, or the application liquid for single-layer type photosensitive layer formation) may for example further contain a surfactant in order to improve dispersibility of the components.

No particular limitations are placed on the method by which each of the application liquids (the application liquid for charge generating layer formation, the application liquid for charge transport layer formation, or the application liquid for single-layer type photosensitive layer formation) is applied so long as the method enables uniform application of the application liquid on or above the conductive substrate. Examples of application methods that can be used include dip coating, spray coating, spin coating, and bar coating.

No particular limitations are placed on the method by which each of the application liquids (the application liquid for charge generating layer formation, the application liquid for charge transport layer formation, or the application liquid for single-layer type photosensitive layer formation) is dried so long as the method enables evaporation of a solvent contained in the application liquid. Examples thereof include heat treatment (hot-air drying) using a high-temperature dryer or a reduced pressure dryer. The heat treatment is for example performed for at least 3 minutes and no greater than 120 minutes at a temperature of at least 40° C. and no greater than 150° C.

The method for producing the photosensitive member may further include either or both of an intermediate layer formation process and a protective layer formation process as necessary. Appropriate known methods are selected for the intermediate layer formation process and the protective layer formation process.

Through the above, the photosensitive member containing the benzidine derivative according to the present embodiment has been described. Through the benzidine derivative according to the present embodiment, crystallization in the photosensitive layer can be inhibited and electrical properties of the photosensitive member can be improved.

EXAMPLES

The following provides more specific description of the present disclosure through use of Examples. However, the present disclosure is not in any way limited by the scope of the Examples.

<1. Photosensitive Member Materials>

A hole transport material and a charge generating material described below were prepared as materials for forming a charge generating layer and a charge transport layer of a multi-layer photosensitive member. A hole transport material, a charge generating material, and an electron transport material described below were prepared as materials for forming a single-layer type photosensitive layer of a single-layer photosensitive member.

<1-1. Hole Transport Material>

The benzidine derivatives HT-1 to HT-6 described in the embodiment were prepared as hole transport materials. The benzidine derivatives HT-1 to HT-6 were synthesized according to the methods described below.

<1-1-1. Synthesis of Benzidine Derivative HT-1>

The benzidine derivative HT-1 described in the embodiment was synthesized through reactions represented by schemes (R-7) to (R-12) shown below. Hereinafter, the reactions represented by the schemes (R-7) to (R-12) may be referred to as reactions R-7 to R-12.

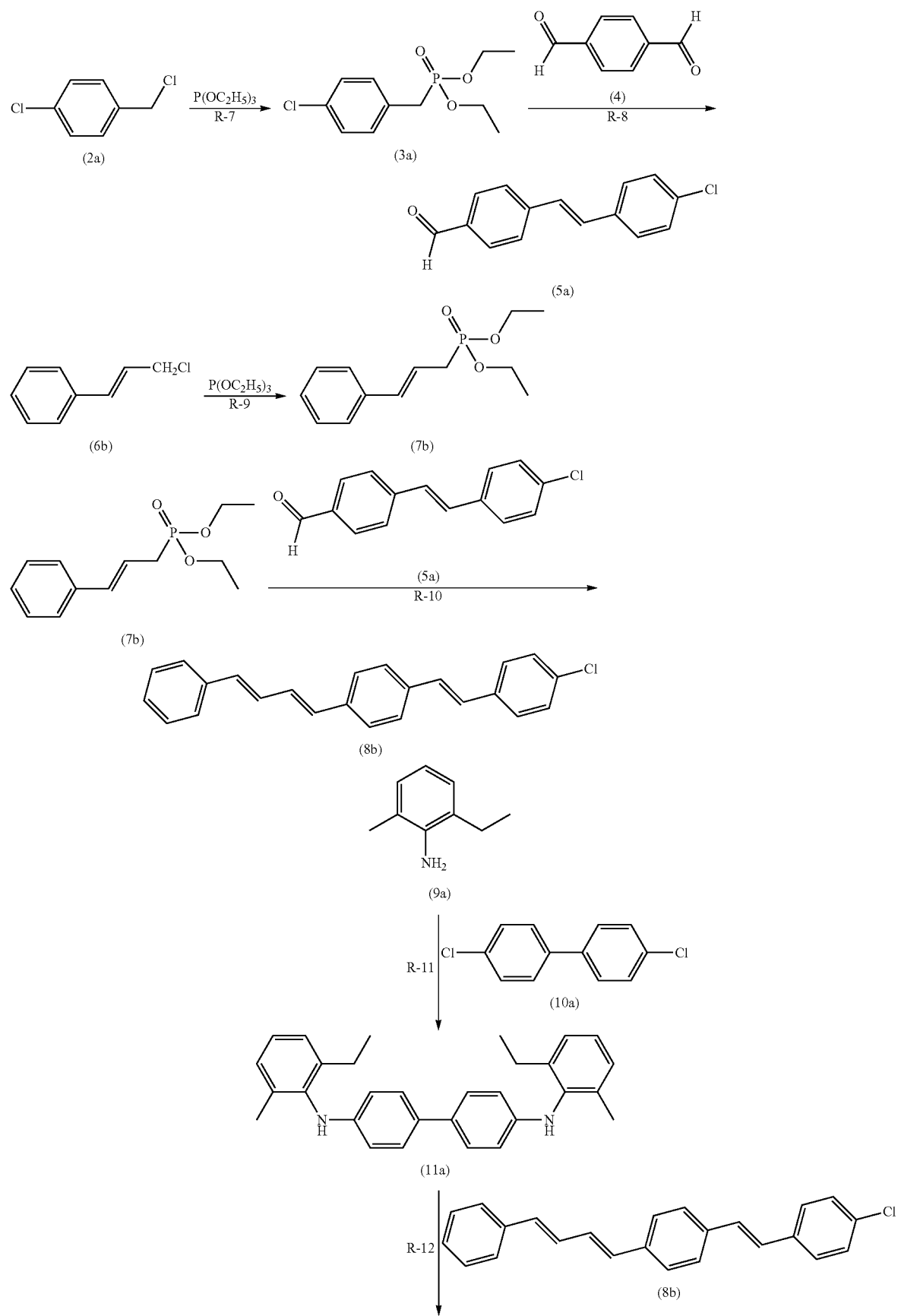

-continued

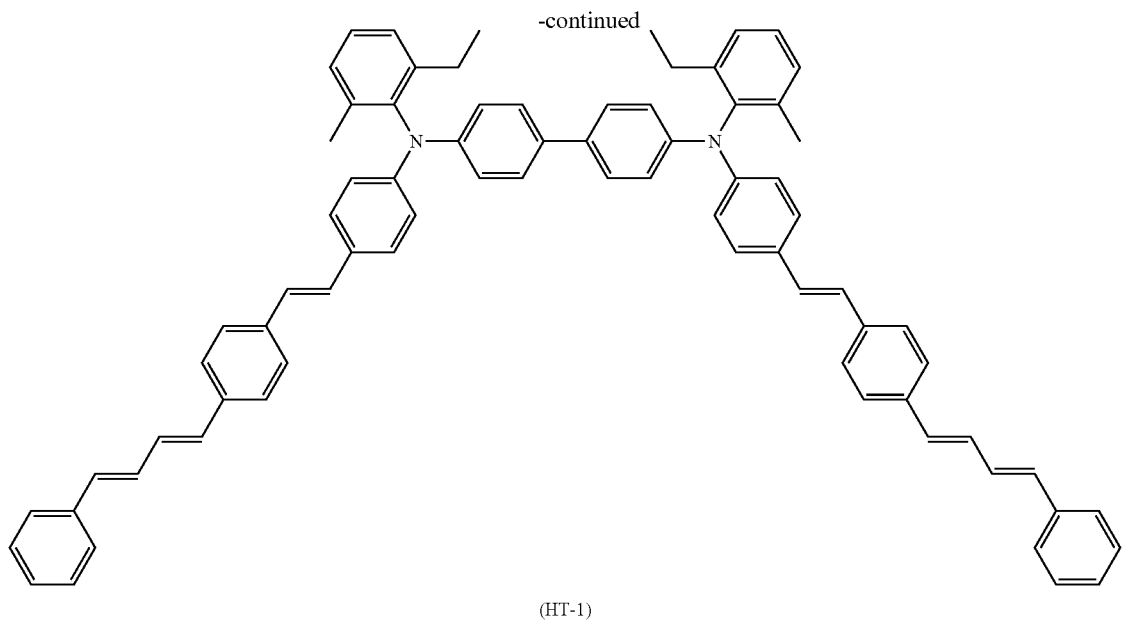

(HT-1)

In the reaction R-7, the compound 2a was caused to react with triethyl phosphite to give the compound 3a. More specifically, the compound 2a (16.1 g, 0.10 mol) and triethyl phosphite (25.0 g, 0.15 mol) were added into a 200 mL flask. The flask contents were stirred at 180° C. for 8 hours and subsequently cooled to room temperature. Next, unreacted triethyl phosphite in the flask contents was evaporated under reduced pressure. Through the above, the compound 3a (mass yield 24.1 g, percentage yield 92 mol %) was obtained as a white liquid.

Next, in the reaction R-8, the compound 3a was caused to react with the compound 4 to give the compound 5a. The reaction R-8 was a Wittig reaction. More specifically, the compound 3a (13.0 g, 0.05 mol) obtained through the reaction R-7 was added into a 500 mL two-necked flask at 0° C. Air in the flask was replaced with argon gas. Next, dried tetrahydrofuran (100 mL) and a solution of the compound 4 (35.0 g, 0.27 mol) in dried tetrahydrofuran (300mL) were added into the flask. The flask contents were stirred for 30 minutes. Next, 28% sodium methoxide (9.3 g, 0.05 mol) was added into the flask. The flask contents were stirred at room temperature for 12 hours. The flask contents were poured into ion exchanged water, and extraction was performed using toluene. A resultant organic layer was washed five times using ion exchanged water and dried using anhydrous sodium sulfate. Next, the solvent contained in the organic layer was evaporated to leave a residue. The resultant residue was purified using a mixture of toluene (20 mL) and methanol (100 mL). Through the above, the compound 5a (mass yield 3.6 g, percentage yield 30 mol %) was obtained as white crystals.

In the reaction R-9, the compound 6b was caused to react with triethyl phosphite to give the compound 7b. More specifically, the compound 6b (15.3 g, 0.100 mol) and triethyl phosphite (25.0 g, 0.150 mol) were added into a 200 mL flask. The flask contents were stirred at 180° C. for 8 hours and subsequently cooled to room temperature. Next, unreacted triethyl phosphite in the flask contents was evaporated under reduced pressure. Through the above, the compound 7b (mass yield 23.2 g, percentage yield 91 mol %) was obtained as a white liquid.

Next, in the reaction R-10, the compound 7b was caused to react with the compound 5a to give the compound 8b. The reaction R-10 was a Wittig reaction. More specifically, the compound 7b (12.8 g, 0.05 mol) obtained through the reaction R-9 was added into a 500 mL two-necked flask at 0° C. Air in the flask was replaced with argon gas. Next, dried tetrahydrofuran (100 mL) and 28% sodium methoxide (9.3 g, 0.05 mol) were added into the flask. The flask contents were stirred for 30 minutes. Next, a solution of the compound 5a (12.2 g, 0.05 mol) obtained through the reaction R-8 in dried tetrahydrofuran (300 mL) was added into the flask. The flask contents were stirred at room temperature for 12 hours. The flask contents were poured into ion exchanged water, and extraction was performed using toluene. A resultant organic layer was washed five times using ion exchanged water and dried using anhydrous sodium sulfate. Next, the solvent contained in the organic layer was evaporated to leave a residue. The resultant residue was purified using a mixture of toluene (20 mL) and methanol (100 mL). Through the above, the compound 8b (mass yield 15.3 g, percentage yield 89 mol %) was obtained as white crystals.

Next, in the reaction R-11, the compound 9a was caused to react with the compound 10a to give the compound ha. The reaction R-11 was a coupling reaction. More specifically, the compound 10a (dichlorobiphenyl, 5.6 g, 0.025 mol), tricyclohexylphosphine (0.066 g, 0.00019 mol), tris (dibenzylideneacetone)dipalladium(0) (0.086 g, 0.000094 mol), sodium tert-butoxide (7.7 g, 0.08 mol), the compound 9a (6.8 g, 0.05 mol), and distilled o-xylene (500 mL) were added into a three-necked flask. Air in the flask was replaced with argon gas. Next, the flask contents were stirred at 120° C. for 5 hours and subsequently cooled to room temperature. The flask contents were washed three times using ion exchanged water to obtain an organic layer. Anhydrous sodium sulfate and activated clay were added to the organic layer to perform drying and adsorption treatment of the organic layer. After drying and adsorption treatment, the organic layer was subjected to reduced pressure evaporation in order to remove o-xylene. Through the above, a residue was obtained. The resultant residue was purified using chloroform and hexane (at a volume ratio of 1:1). Through the above, the compound ha (mass yield 7.5 g, percentage yield 71 mol %) was obtained as a solid.

Next, in the reaction R-12, the compound ha was caused to react with the compound 8b to give the benzidine derivative HT-1. The reaction R-12 was a coupling reaction. More specifically, the compound ha (10.5 g, 0.025 mol) obtained through the reaction R-11, tricyclohexylphosphine (0.066 g, 0.00019 mol), tris(dibenzylideneacetone)dipalladium(0) (0.086 g, 0.000094 mol), sodium tert-butoxide (7.7 g, 0.08 mol), the compound 8b (17.0 g, 0.05 mol) obtained through the reaction R-10, and distilled o-xylene (500 mL) were added into a three-necked flask. Air in the flask was replaced with argon gas. Next, the flask contents were stirred at 120° C. for 5 hours and subsequently cooled to room temperature. The flask contents were washed three times using ion exchanged water to obtain an organic layer. Anhydrous sodium sulfate and activated clay were added to the organic layer to perform drying and adsorption treatment of the organic layer. After drying and adsorption treatment, the organic layer was subjected to reduced pressure evaporation in order to remove o-xylene. Through the above, a residue was obtained. The resultant residue was purified by silica gel column chromatography using chloroform and hexane (at a volume ratio of 1:1) as a developing solvent. Through the above, the benzidine derivative HT-1 (mass yield 17.2 g, percentage yield 67 mol %) was obtained.

<1-1-2. Synthesis of Benzidine Derivatives HT-2 to HT-6>

The benzidine derivatives HT-2 to HT-6 described in the embodiment were synthesized in the same manner as in the synthesis of the benzidine derivative HT-1 except the following changes. The number of moles of each of raw materials used in the synthesis of the benzidine derivatives HT-2 to HT-6 was the same as the number of moles of the corresponding raw material used in the synthesis of the benzidine derivative HT-1.

The raw materials shown in Table 1 (compounds 9a, 9b, 9c, 9d, and 9e) were used in the reaction R-11 in the synthesis of the benzidine derivatives HT-2 to HT-6, whereas the compound 9a was used in the synthesis of the benzidine derivative HT-1. As a result, reaction products shown in Table 1 (compounds 11a, 11b, 11c, 11d, and 11e) were obtained through the reaction R-11. The percentage yield of each reaction product obtained through the reaction R-11 is shown in Table 1.

The raw materials shown in Table 1 (compounds 11a, 11b, 11c, 11d, and 11e) were used in the reaction R-12 in the synthesis of the benzidine derivatives HT-2 to HT-6, whereas the compound 11a was used in the synthesis of the benzidine derivative HT-1. Furthermore, the raw materials shown in Table 1 (compounds 8a, 8b, and 8c) were used in the reaction R-12 in the synthesis of the benzidine derivatives HT-2 to HT-6, whereas the compound 8b was used in the synthesis of the benzidine derivative HT-1. As a result, the benzidine derivatives HT-2 to HT-6 were obtained through the reaction R-12, rather than the benzidine derivative HT-1. The percentage yield of each of the benzidine derivatives HT-2 to HT-6 obtained through the reaction R-12 is shown in Table 1.

The compounds 9a, 9b, 9c, 9d, 9e, 11a, 11b, 11c, 11d, 11e, 8a, 8b, and 8c in Table 1 are respectively represented by chemical formulae (9a), (9b), (9c), (9d), (9e), (11a), (11b), (11c), (11d), (11e), (8a), (8b), and (8c) shown below.

TABLE 1

| Benzidine derivative | Reaction R-11 | | | Reaction R-12 | | | |
| --- | --- | --- | --- | --- | --- | --- | --- |
| | Raw material | Reaction product | Yield [mol %] | Raw material | Raw material | Reaction product | Yield [mol %] |
| HT-1 | 9a | 11a | 71 | 11a | 8b | HT-1 | 67 |
| HT-2 | 9a | 11a | 71 | 11a | 8a | HT-2 | 70 |
| HT-3 | 9b | 11b | 70 | 11b | 8a | HT-3 | 62 |
| HT-4 | 9c | 11c | 72 | 11c | 8c | HT-4 | 65 |
| HT-5 | 9d | 11d | 65 | 11d | 8b | HT-5 | 65 |
| HT-6 | 9e | 11e | 60 | 11e | 8a | HT-6 | 60 |

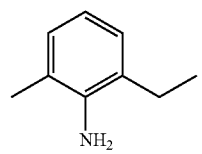

(9a)

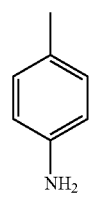

(9b)

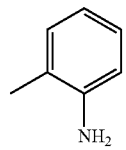

(9c)

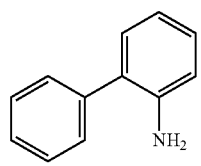

(9d)

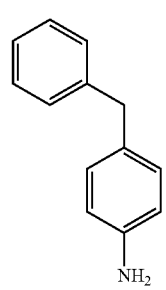

(9e)

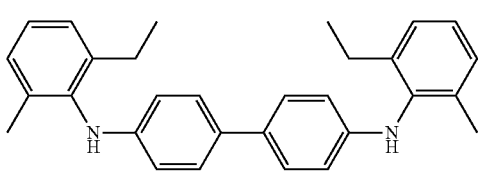

(11a)

-continued

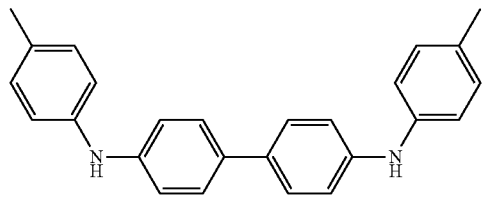
(11b)

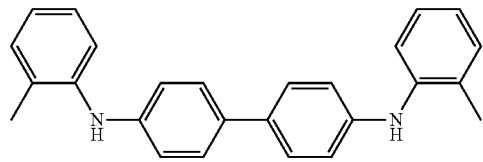
(11c)

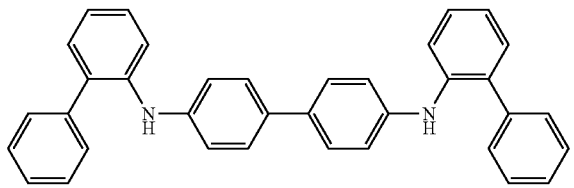
(11d)

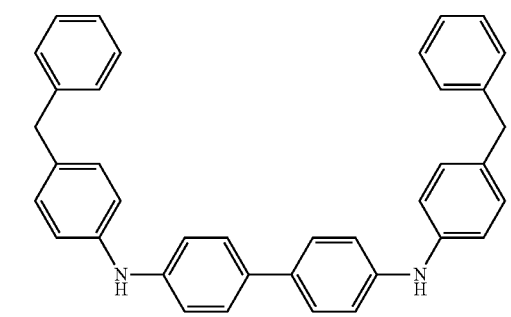
(11e)

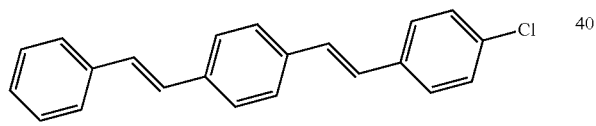
(8a)

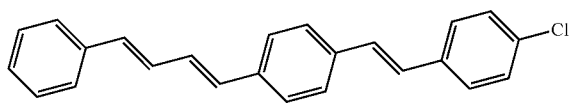
(8b)

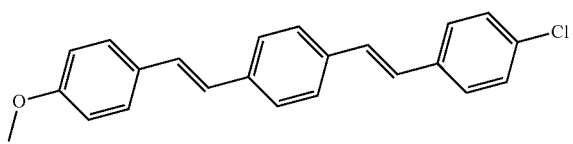
(8c)

The raw materials (compounds 8a and 8c) used in the reaction R-12 were synthesized in the same manner as in the synthesis of the compound 8b except the following changes. The raw material used in the reaction R-9 was changed from the compound 6b to the raw material shown in Table 2 (compound 6a or 6c). As a result, a reaction product shown in Table 2 (compound 7a or 7c) was obtained through the reaction R-9, rather than the compound 7b. The percentage yield of each reaction product obtained through the reaction R-9 is shown in Table 2. Next, the raw material used in the reaction R-10 was changed from the compound 7b used in the synthesis of the compound 8b to the raw material shown in Table 2 (compound 7a or 7c). As a result, a reaction product shown in Table 2 (compound 8a or 8c) was obtained through the reaction R-10, rather than the compound 8b. The percentage yield of each reaction product obtained through the reaction R-10 is shown in Table 2.

The compounds 6a, 6b, 6c, 7a, 7b, and 7c in Table 2 are respectively represented by the chemical formulae (6a), (6b), (6c), (7a), (7b), and (7c).

TABLE 2

| Raw material of Reaction R-12 | Reaction R-9 | | | Reaction R-10 | | |
|---|---|---|---|---|---|---|
| | Raw material | Reaction product | Yield [mol %] | Raw material | Reaction product | Yield [mol %] |
| 8b | 6b | 7b | 91 | 7b | 8b | 89 |
| 8a | 6a | 7a | 90 | 7a | 8a | 85 |
| 8c | 6c | 7c | 85 | 7c | 8c | 82 |

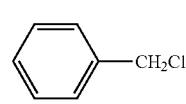
(6a)

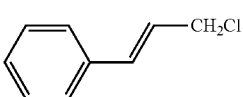
(6b)

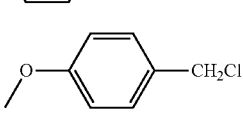
(6c)

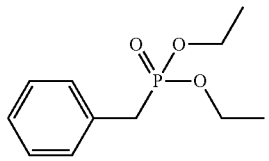
(7a)

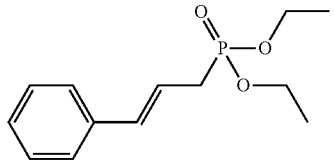
(7b)

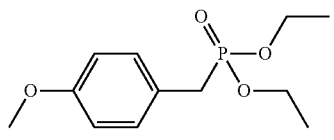

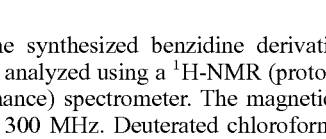
(7c)

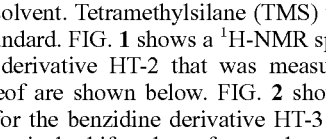

Figure 1:
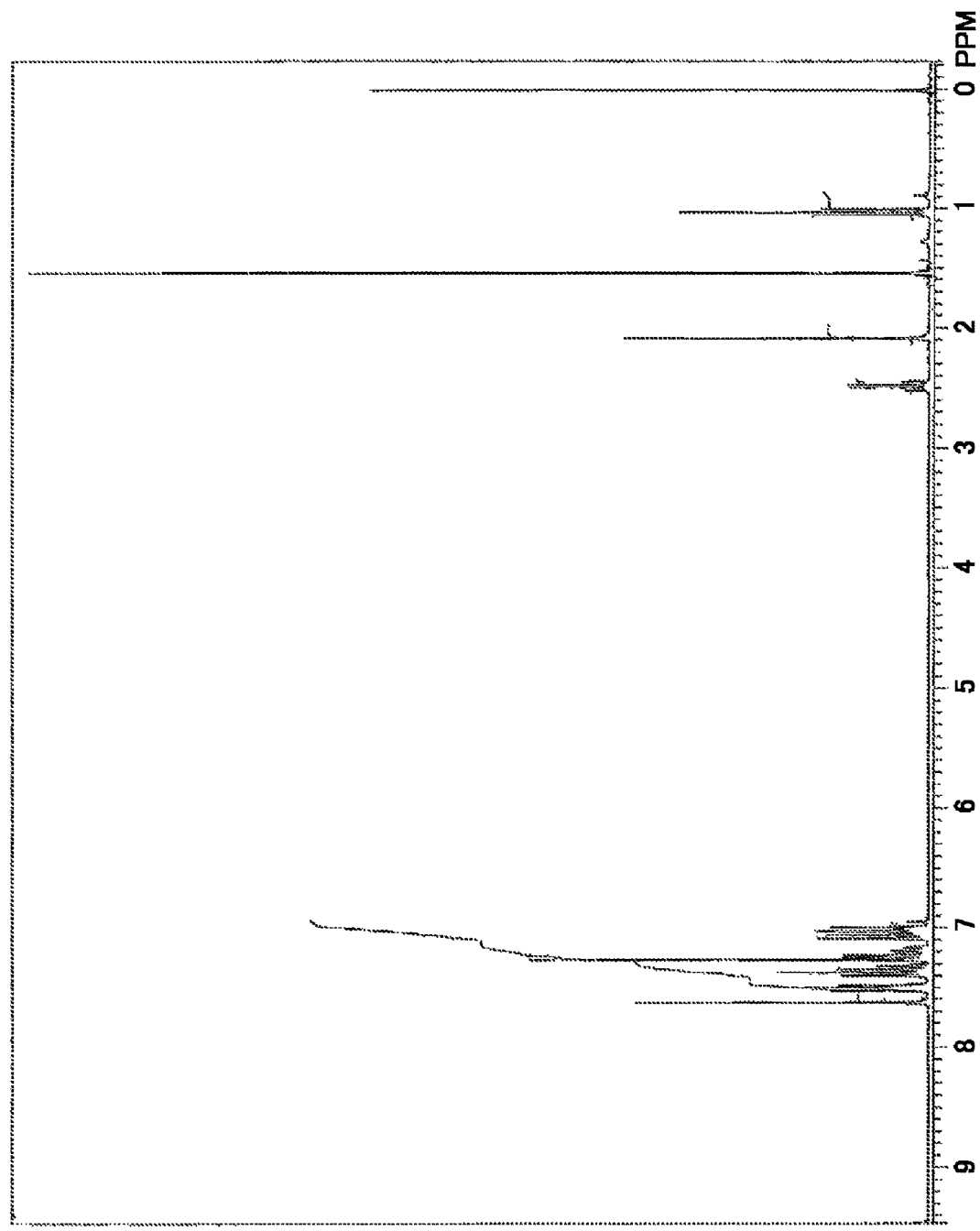
FIG. 1 is a $^1$H-NMR spectrum for a benzidine derivative represented by chemical formula (HT-2) according to an embodiment of the present disclosure.

Next, the synthesized benzidine derivatives HT-2 and HT-3 were analyzed using a $^1$H-NMR (proton nuclear magnetic resonance) spectrometer. The magnetic field strength was set to 300 MHz. Deuterated chloroform (CDCl$_3$) was used as a solvent. Tetramethylsilane (TMS) was used as an internal standard. FIG. 1 shows a $^1$H-NMR spectrum for the benzidine derivative HT-2 that was measured. Chemical shifts thereof are shown below. FIG. 2 shows a $^1$H-NMR spectrum for the benzidine derivative HT-3 that was measured. Chemical shifts thereof are shown below. The $^1$H-NMR spectra and the chemical shifts were used to confirm that the benzidine derivatives HT-2 and HT-3 had structures represented by the chemical formulae (HT-2) and (HT-3), respectively.

Benzidine derivative HT-2: $^1$H-NMR (300 MHz, CDCl$_3$) δ 1.0 (t, 6H), 2.1 (s, 6H), 2.4 (q, 4H), 6.9-7.7 (m, 48H).

Benzidine derivative HT-3: $^1$H-NMR (300 MHz, CDCl$_3$) δ 2.3 (s, 6H), 6.6-7.4 (m, 50H).

<1-1-3. Preparation of Benzidine Derivatives HT-A and HT-B>

Benzidine derivatives represented by chemical formulae (HT-A) and (HT-B) shown below were also prepared. Hereinafter, the benzidine derivatives represented by the chemical formulae (HT-A) and (HT-B) may be referred to as benzidine derivatives HT-A and HT-B, respectively.

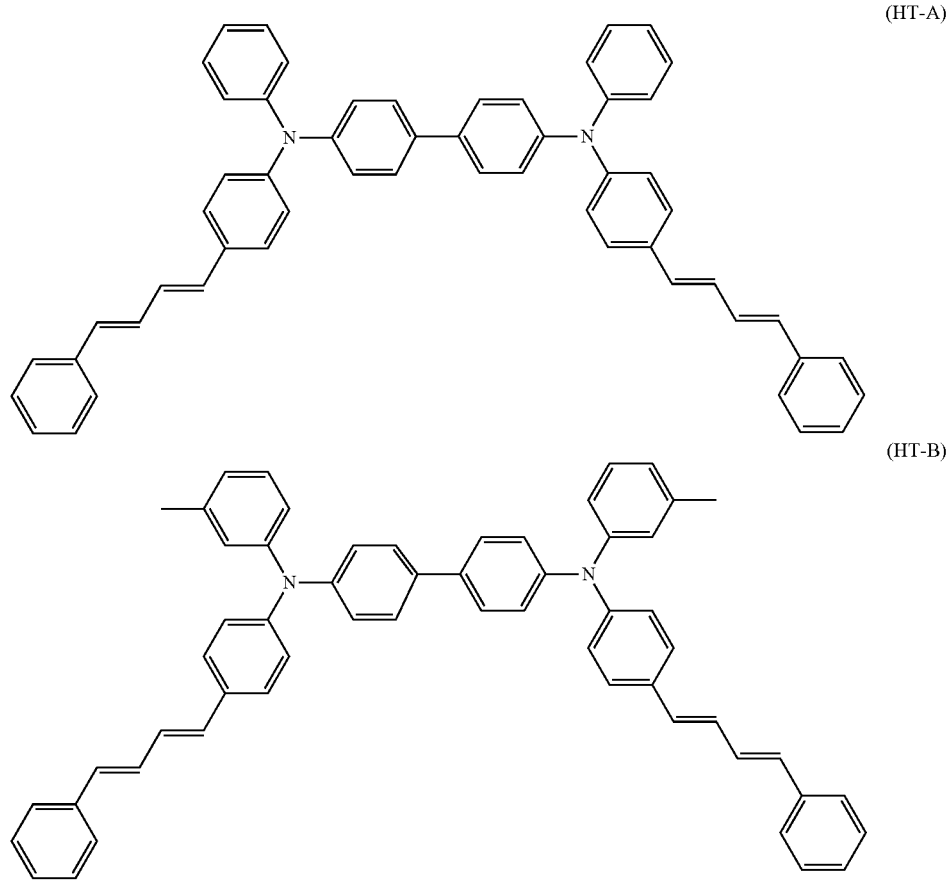

<1-2. Charge Generating Material>

Compounds CG-1X and CG-2Y were prepared as charge generating materials. The compound CG-1X was metal-free phthalocyanine represented by the chemical formula (CG-1) described in the embodiment. The compound CG-1X had an X-form crystalline structure.

The compound CG-2Y was titanyl phthalocyanine represented by the chemical formula (CG-2) described in the embodiment. The compound CG-2Y had a Y-form crystalline structure.

<1-3. Electron Transport Material>

The compounds ET-1 and ET-3 described in the embodiment were prepared as electron transport materials to be contained in single-layer type photosensitive layers of single-layer photosensitive members.

<2. Multi-Layer Photosensitive Member Production>

Multi-layer photosensitive members A-1 to A-6 and B-1 to B-2 were produced using the above-described materials for photosensitive layer formation.

<2-1. Production of Multi-Layer Photosensitive Member A-1>

First, surface-treated titanium oxide ("test sample SMT-02", product of Tayca Corporation, number average primary particle size: 10 nm) was prepared. The surface-treated titanium oxide was prepared as described below. Titanium oxide was surface-treated using alumina and silica. The titanium oxide surface-treated with alumina and silica was further surface-treated using methyl hydrogen polysiloxane during wet dispersion.

Next, an application liquid for undercoat layer formation was prepared. More specifically, the surface-treated titanium oxide (2.8 parts by mass), copolyamide resin ("DAIAMID X4685", product of Daicel-Evonik Ltd., 1 part by mass), ethanol (10 parts by mass) as a solvent, and butanol (2 parts by mass) as a solvent were added into a vessel. The vessel contents were mixed for 5 hours using a bead mill in order to disperse the materials in the mixed solvent. Through the above, an application liquid for undercoat layer formation was obtained.

Next, an undercoat layer was formed. More specifically, the resultant application liquid for undercoat layer formation was filtered using a filter having a pore size of 5 μm. Next, the application liquid for undercoat layer formation was applied to a surface of a conductive substrate—an aluminum drum-shaped support (diameter: 30 mm, total length: 238.5 mm)—by dip coating. Next, the applied application liquid for undercoat layer formation was heated at 130° C. for 30 minutes. Through the above, an undercoat layer (film thickness: 1.5 μm) was formed on the conductive substrate.

Next, an application liquid for charge generating layer formation was prepared. More specifically, the compound CG-2Y (1 part by mass) as a charge generating material, polyvinyl butyral resin ("Denka Butyral #6000EP", product of Denka Company Limited, 1 part by mass) as a base resin, propylene glycol monomethyl ether (40 parts by mass) as a dispersion medium, and tetrahydrofuran (40 parts by mass) as a dispersion medium were added into a vessel. The vessel contents were mixed for 2 hours using a bead mill in order to disperse the materials in the mixed dispersion medium. Through the above, an application liquid for charge generating layer formation was obtained. Next, the resultant application liquid for charge generating layer formation was filtered using a filter having a pore size of 3 μm. Thereafter, the application liquid for charge generating layer formation was applied to the conductive substrate having the undercoat layer by dip coating. Next, the applied application liquid for charge generating layer formation was dried at 50° C. for 5 minutes. Through the above process, a charge generating layer (film thickness: 0.3 μm) was formed on the undercoat layer.

Next, an application liquid for charge transport layer formation was prepared. More specifically, the benzidine derivative HT-1 (70 parts by mass) as a hole transport material, bisphenol Z-form polycarbonate resin ("Panlite (registered Japanese trademark) TS-2050", product of Teijin Limited, viscosity average molecular weight: 50,000, 100 parts by mass) as a binder resin, BHT (di(tert-butyl)p-cresol, 5 parts by mass) as an additive, tetrahydrofuran (430 parts by mass) as a solvent, and toluene (430 parts by mass) as a solvent were added into a vessel. The vessel contents were mixed in order to dissolve the materials in the mixed solvent. Through the above, an application liquid for charge transport layer formation was obtained. Next, the resultant application liquid for charge transport layer formation was applied to the conductive substrate having the undercoat layer and the charge generating layer in the same manner as in the application of the application liquid for charge generating layer formation. Next, the applied application liquid for charge transport layer formation was dried at 130° C. for 30 minutes. Through the above process, a charge transport layer (film thickness: 20 μm) was formed on the charge generating layer. As a result, the multi-layer photosensitive member A-1 was obtained.

<2-2. Production of Multi-Layer Photosensitive Members A-2 to A-6 and B-1 to B-2>

The multi-layer photosensitive members A-2 to A-6 and B-1 to B-2 were produced in the same manner as in the production of the multi-layer photosensitive member A-1 except the following changes. The benzidine derivative HT-1 used as the hole transport material in the production of the multi-layer photosensitive member A-1 was changed to each of the hole transport materials shown in Table 3.

<3. Single-Layer Photosensitive Member Production>

The materials for photosensitive layer formation were used to produce single-layer photosensitive members C-1 to C-9 and D-1 to D-6.

<3-1. Production of Single-Layer Photosensitive Member C-1>

The compound CG-1X (5 parts by mass) as a charge generating material, the benzidine derivative HT-1 (80 parts by mass) as a hole transport material, the compound ET-1 (50 parts by mass) as an electron transport material, bisphenol Z-form polycarbonate resin ("Panlite (registered Japanese trademark) TS-2050", product of Teijin Limited, viscosity average molecular weight: 50,000, 100 parts by mass) as a binder resin, and tetrahydrofuran (800 parts by mass) as a solvent were added into a vessel. The vessel contents were mixed for 50 hours using a ball mill in order to disperse the materials in the solvent. Through the above, an application liquid for single-layer type photosensitive layer formation was obtained. The application liquid for single-layer type photosensitive layer formation was applied to a conductive substrate—an aluminum drum-shaped support (diameter: 30 mm, total length: 238.5 mm)—by dip coating. The applied application liquid for single-layer type photosensitive layer formation was hot-air dried at 100° C. for 30 minutes. Through the above, a single-layer type photosensitive layer (film thickness: 25 μm) was formed on the conductive substrate. As a result, the single-layer photosensitive member C-1 was obtained.

<3-2. Production of Single-Layer Photosensitive Members C-2 to C-9 and D-1 to D-6>

The single-layer photosensitive members C-2 to C-9 and D-1 to D-6 were produced in the same manner as in the production of the single-layer photosensitive member C-1 except the following changes. The compound CG-1X used as the charge generating material in the production of the single-layer photosensitive member C-1 was changed to each of the charge generating materials shown in Table 4. The benzidine derivative HT-1 used as the hole transport material in the production of the single-layer photosensitive member C-1 was changed to each of the hole transport materials shown in Table 4. The compound ET-1 used as the electron transport material in the production of the single-layer photosensitive member C-1 was changed to each of the electron transport materials shown in Table 4.

<4. Evaluation of Multi-Layer Photosensitive Member Electrical Properties>

With respect to each of the multi-layer photosensitive members A-1 to A-6 and B-1 to B-2 produced as described above, electrical properties of the photosensitive member were evaluated. The evaluation of the electrical properties was performed under environmental conditions of 23° C. and 60% RH. First, the surface of the multi-layer photosensitive member was charged to a negative polarity using a drum sensitivity test device (product of Gen-Tech, Inc.). Charging conditions were a multi-layer photosensitive member rotation speed of 31 rpm and an inflow current of −8 μA. The surface potential of the multi-layer photosensitive member was measured immediately after charging. The thus measured surface potential of the multi-layer photosensitive member was taken to be an initial potential ($V_0$, unit: V). Next, a band pass filter was used to obtain monochromatic light (wavelength: 780 nm, half-width: 20 nm, light intensity: 0.4 μJ/cm$^2$) from white light emitted by a halogen lamp. The obtained monochromatic light was irradiated onto the surface of the multi-layer photosensitive member. The surface potential of the multi-layer photosensitive member was measured once 0.5 seconds had elapsed after completion of the irradiation. The measured surface potential was taken to be a residual potential ($V_L$, unit: V). The initial electric potential ($V_0$) and the residual potential ($V_L$) of the multi-layer photosensitive members that were measured are shown in Table 3. It should be noted that a residual potential ($V_L$) having a small absolute value indicates excellent electrical properties.

<5. Evaluation of Single-Layer Photosensitive Member Electrical Properties>

With respect to each of the single-layer photosensitive members C-1 to C-9 and D-1 to D-6 produced as described above, electrical properties of the photosensitive member were evaluated. The evaluation of the electrical properties was performed under environmental conditions of 23° C. and 60% RH. First, the surface of the single-layer photosensitive member was charged to a positive polarity using a drum sensitivity test device (product of Gen-Tech, Inc.). Charging conditions were a single-layer photosensitive member rotation speed of 31 rpm and an inflow current of +8 μA. The surface potential of the single-layer photosensitive member was measured immediately after charging. The thus measured surface potential of the single-layer photosensitive member was taken to be an initial potential ($V_0$, unit: V). Next, a band pass filter was used to obtain monochromatic light (wavelength: 780 nm, half-width: 20 nm, light intensity: 1.5 μJ/cm$^2$) from white light emitted by a halogen lamp. The obtained monochromatic light was irradiated onto the surface of the single-layer photosensitive member. The surface potential of the single-layer photosensitive member was measured once 0.5 seconds had elapsed after completion of the irradiation. The measured surface potential was taken to be a residual potential ($V_L$, unit: V). The initial electric potential ($V_0$) and the residual potential ($V_L$) of the single-layer photosensitive members that were measured are shown in Table 4. It should be noted that a residual potential ($V_L$) having a small absolute value indicates excellent electrical properties.

<6. Crystallization Resistance Evaluation>

With respect to each of the multi-layer photosensitive members A-1 to A-6 and B-1 to B-2, and each of the single-layer photosensitive members C-1 to C-9 and D-1 to D-6, the entire surface region of the photosensitive member (photosensitive layer) was observed using unaided eyes. Through the above observation, it was confirmed whether or not a crystallized portion was present in the photosensitive layer. With respect to each of the multi-layer photosensitive members and the single-layer photosensitive members, photosensitive layer crystallization resistance of the photosensitive member was evaluated based on the confirmation result in accordance with the following evaluation standard. Results of the photosensitive layer crystallization resistance are shown in Tables 3 and 4.

(Crystallization Resistance Evaluation Standard)
G (Good): No crystallized portion observed
P (Poor): Crystallized portion slightly observed
PP (Particularly Poor): Crystallized portion observed The results of the evaluations of electrical properties and crystallization resistance of the multi-layer photosensitive members are shown in Table 3. The results of the evaluations of electrical properties and crystallization resistance of the single-layer photosensitive members are shown in Table 4. In Tables 3 and 4, CGM, HTM, ETM, $V_0$, and $V_L$ represent charge generating material, hole transport material, electron transport material, initial electric potential, and residual potential, respectively. With respect to each of the multi-layer photosensitive member B-1 and the single-layer photosensitive members D-1 to D-6, the photosensitive member could not be charged due to crystallization in the photosensitive layer, and therefore the initial electric potential ($V_0$) and the residual potential ($V_L$) were unmeasurable.

TABLE 3

| | Multi-layer photosensitive member | HTM | Electrical properties $V_0$ (V) | $V_L$ (V) | Crystallization resistance Evaluation |
|---|---|---|---|---|---|
| Example 1 | A-1 | HT-1 | −700 | −75 | G |
| Example 2 | A-2 | HT-2 | −700 | −82 | G |
| Example 3 | A-3 | HT-3 | −700 | −85 | G |
| Example 4 | A-4 | HT-4 | −700 | −94 | G |
| Example 5 | A-5 | HT-5 | −700 | −80 | G |
| Example 6 | A-6 | HT-6 | −700 | −86 | G |
| Comparative Example 1 | B-1 | HT-A | Unmeasurable | Unmeasurable | PP |
| Comparative Example 2 | B-2 | HT-B | −700 | −122 | P |

TABLE 4

| | Single-layer photosensitive member | CGM | HTM | ETM | Electrical properties $V_0$ (V) | $V_L$ (V) | Crystallization resistance Evaluation |
|---|---|---|---|---|---|---|---|
| Example 7 | C-1 | CG-1X | HT-1 | ET-1 | +698 | +110 | G |
| Example 8 | C-2 | CG-1X | HT-1 | ET-3 | +700 | +114 | G |
| Example 9 | C-3 | CG-2Y | HT-1 | ET-3 | +700 | +106 | G |
| Example 10 | C-4 | CG-1X | HT-2 | ET-1 | +700 | +115 | G |
| Example 11 | C-5 | CG-1X | HT-2 | ET-3 | +699 | +117 | G |
| Example 12 | C-6 | CG-2Y | HT-2 | ET-3 | +699 | +111 | G |
| Example 13 | C-7 | CG-1X | HT-3 | ET-1 | +700 | +114 | G |
| Example 14 | C-8 | CG-1X | HT-3 | ET-3 | +699 | +117 | G |
| Example 15 | C-9 | CG-2Y | HT-3 | ET-3 | +700 | +110 | G |
| Comparative Example 3 | D-1 | CG-1X | HT-A | ET-1 | Unmeasurable | Unmeasurable | PP |

TABLE 4-continued

| Single-layer photosensitive member | CGM | HTM | ETM | Electrical properties | | Crystallization resistance Evaluation |
| --- | --- | --- | --- | --- | --- | --- |
| | | | | $V_0$ (V) | $V_L$ (V) | |
| Comparative Example 4 D-2 | CG-1X | HT-A | ET-3 | Unmeasurable | Unmeasurable | PP |
| Comparative Example 5 D-3 | CG-2Y | HT-A | ET-3 | Unmeasurable | Unmeasurable | PP |
| Comparative Example 6 D-4 | CG-1X | HT-B | ET-1 | Unmeasurable | Unmeasurable | PP |
| Comparative Example 7 D-5 | CG-1X | HT-B | ET-3 | Unmeasurable | Unmeasurable | PP |
| Comparative Example 8 D-6 | CG-2Y | HT-B | ET-3 | Unmeasurable | Unmeasurable | PP |

The photosensitive layer of each of the multi-layer photosensitive members A-1 to A-6 and the single-layer photosensitive members C-1 to C-9 contained the benzidine derivative 1 (more specifically, any of the benzidine derivatives HT-1 to HT-6) as a hole transport material. Consequently, as is clear from Tables 3 and 4, these photosensitive members were evaluated as good in terms of the photosensitive layer crystallization resistance, and crystallization was inhibited in the photosensitive layers thereof. Furthermore, these photosensitive members had a residual potential ($V_L$) with a small absolute value and were excellent in electrical properties.

On the other hand, the photosensitive layer of each of the multi-layer photosensitive members B-1 to B-2 and the single-layer photosensitive members D-1 to D-6 did not contain the benzidine derivative 1 as a hole transport material. Consequently, as is clear from Tables 3 and 4, these photosensitive members were evaluated as poor or particularly poor in terms of the photosensitive layer crystallization resistance, and crystallization was observed in the photosensitive layers thereof. Furthermore, these photosensitive members had a residual potential ($V_L$) with a large absolute value or could not be charged due to crystallization in the photosensitive layers thereof.

The evaluation results have proved that the benzidine derivative 1, when contained in a photosensitive layer of a photosensitive member, can inhibit crystallization in the photosensitive layer and improve electrical properties of the photosensitive member. The evaluation results have also proved that a photosensitive member including a photosensitive layer containing the benzidine derivative 1 can inhibit crystallization of the photosensitive layer and have excellent electrical properties.

What is claimed is:

1. An electrophotographic photosensitive member comprising a conductive substrate and a photosensitive layer, wherein
the photosensitive layer contains at least a charge generating material and a benzidine derivative represented by general formula (1) shown below as a hole transport material,

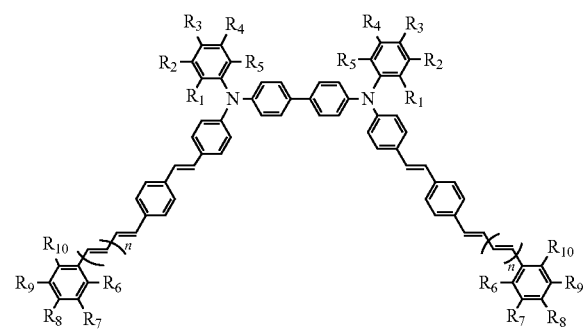

(1)

wherein in the general formula (1), $R_1$, $R_2$, $R_3$, $R_4$, $R_5$, $R_6$, $R_7$, $R_8$, $R_9$, and $R_{10}$ each represent, independently of one another, a hydrogen atom, a halogen atom, an optionally substituted alkyl group having a carbon number of at least 1 and no greater than 6, an optionally substituted alkoxy group having a carbon number of at least 1 and no greater than 6, or an optionally substituted aryl group having a carbon number of at least 6 and no greater than 14, and n represents an integer of at least 0 and no greater than 2.

2. The electrophotographic photosensitive member according to claim 1, comprising, as the photosensitive layer:
a charge generating layer containing the charge generating material and a charge transport layer containing the hole transport material; or
a single-layer type photosensitive layer containing the charge generating material and the hole transport material, wherein
the charge generating material is titanyl phthalocyanine having a Y-form crystal structure.

3. The electrophotographic photosensitive member according to claim 1, wherein
the photosensitive layer is a single-layer type photosensitive layer,
the single-layer type photosensitive layer contains the charge generating material, the hole transport material, and an electron transport material, and
the electron transport material is a compound represented by general formula (12) shown below

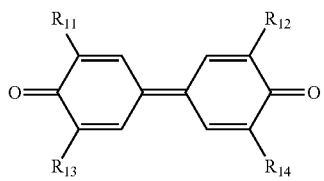

where in the general formula (12), $R_{11}$, $R_{12}$, $R_{13}$, and $R_{14}$ each represent, independently of one another, a hydrogen atom, a cyano group, an optionally substituted alkyl group, an optionally substituted alkenyl group, an optionally substituted alkoxy group, an optionally substituted alkoxycarbonyl group, an optionally substituted aryl group, or an optionally substituted heterocyclic group.

4. The electrophotographic photosensitive member according to claim 1, wherein in the general formula (1), $R_6$, $R_7$, $R_8$, $R_9$, and $R_{10}$ each represent a hydrogen atom.

5. The electrophotographic photosensitive member according to claim 1, wherein in the general formula (1), n represents 1 or 2.

6. The electrophotographic photosensitive member according to claim 1, wherein in the general formula (1), $R_1$, $R_2$, $R_3$, $R_4$, and $R_5$ each represent, independently of one another, a hydrogen atom, an alkyl group having a carbon number of at least 1 and no greater than 6 and optionally having an aryl group having a carbon number of at least 6 and no greater than 14, or an aryl group having a carbon number of at least 6 and no greater than 14, $R_6$, $R_7$, $R_8$, $R_9$, and $R_{10}$ each represent, independently of one another, a hydrogen atom or an alkoxy group having a carbon number of at least 1 and no greater than 6, and n represents 0 or 1.

7. The electrophotographic photosensitive member according to claim 1, wherein the benzidine derivative represented by the general formula (1) is a benzidine derivative represented by chemical formula (HT-1), (HT-2), (HT-3), (HT-4), (HT-5), or (HT-6) shown below

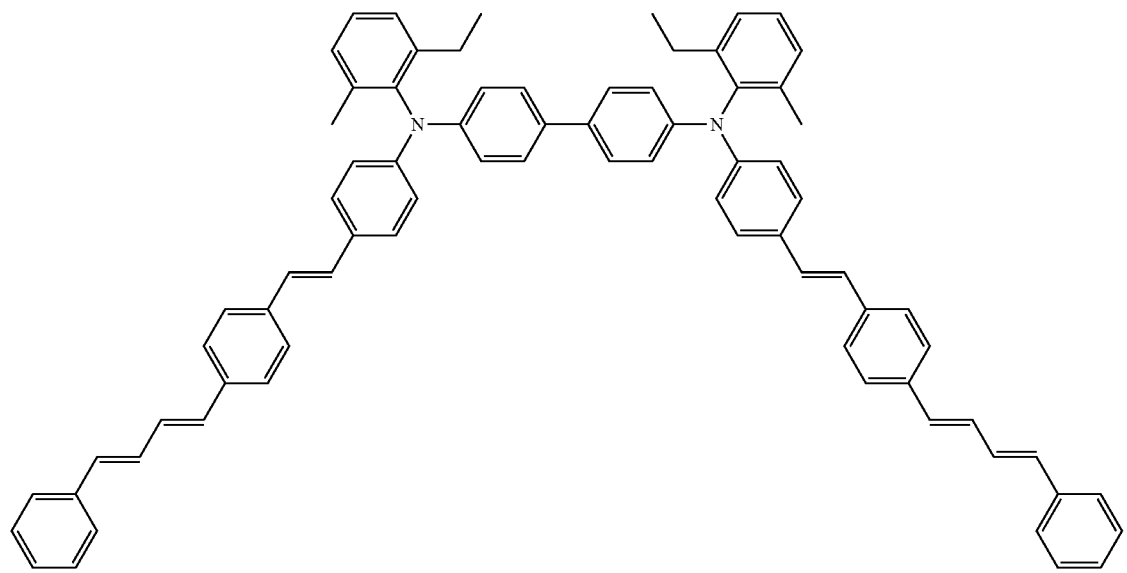

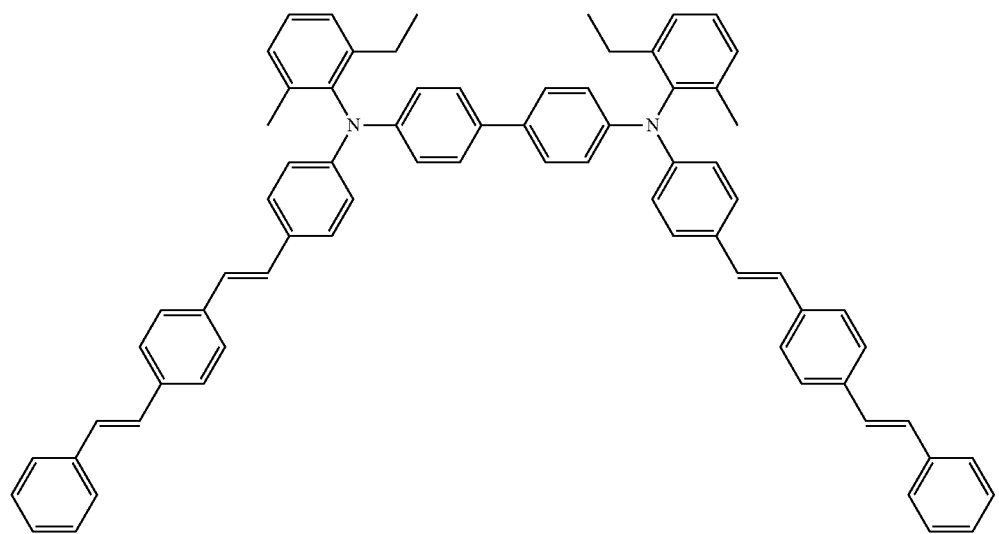
(HT-2)
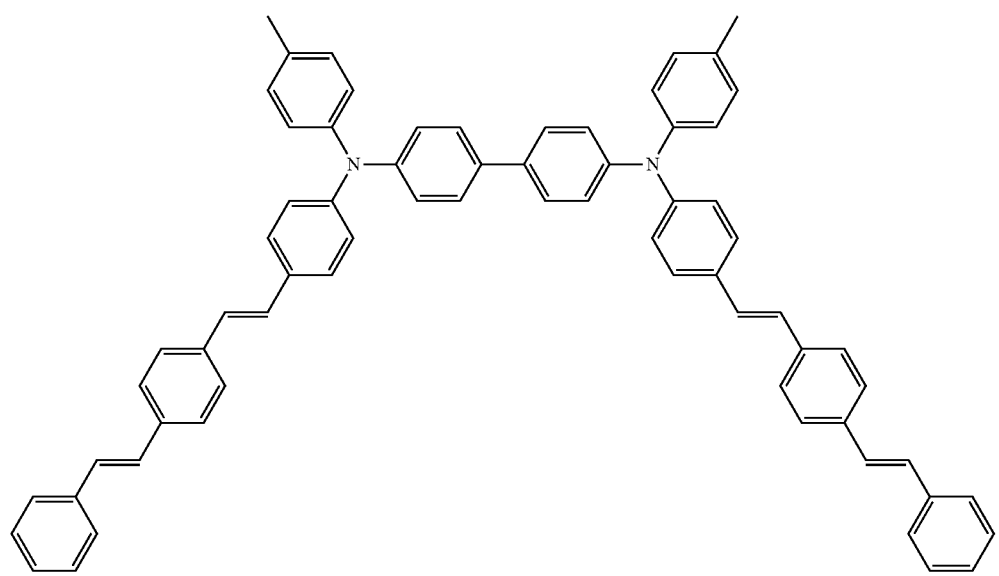
(HT-3)

(HT-4)
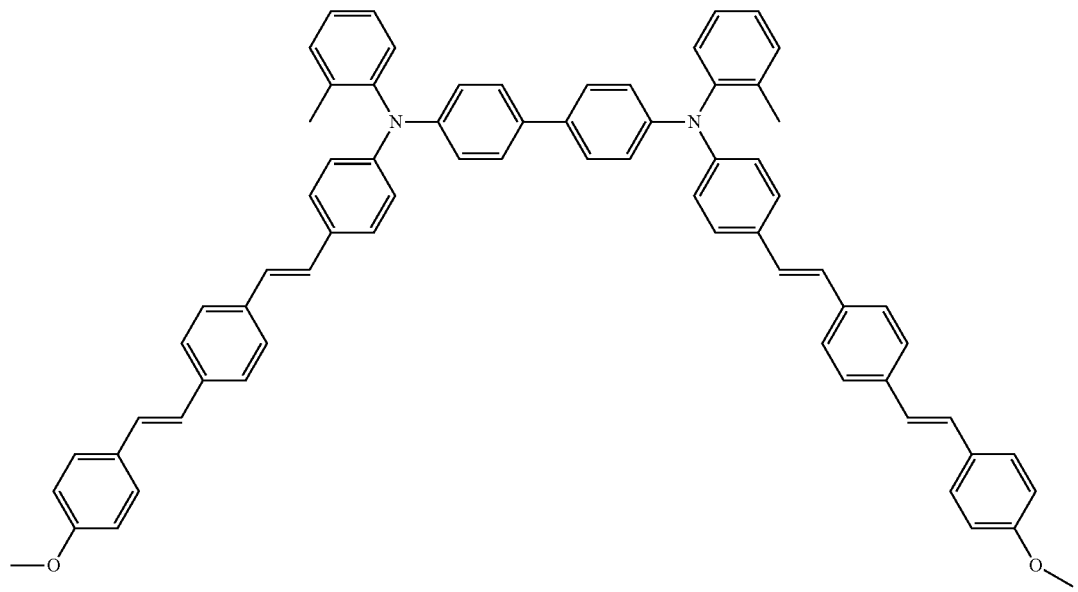
(HT-5)
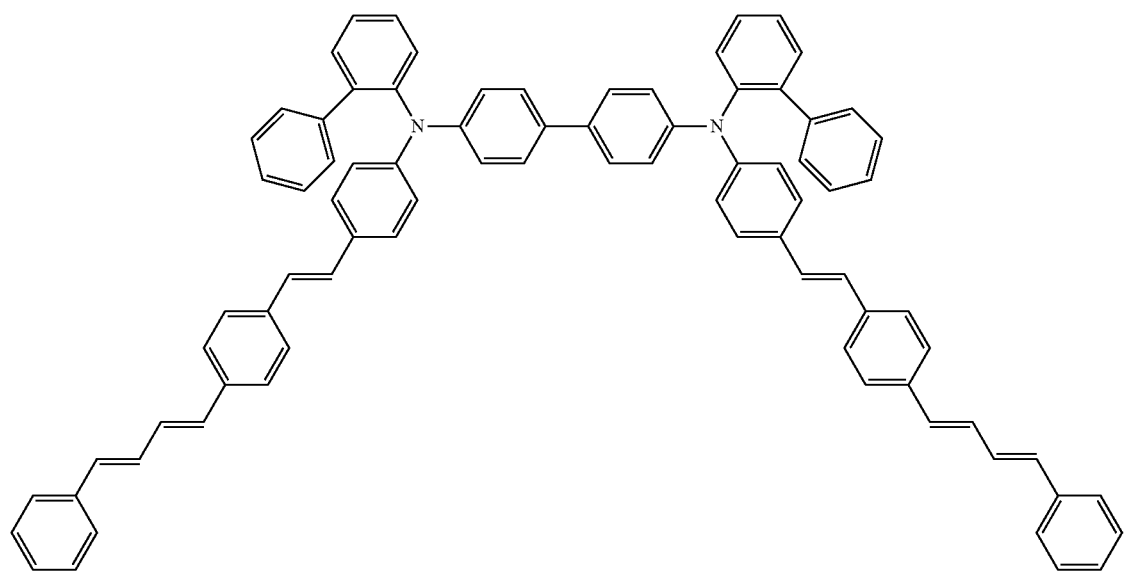

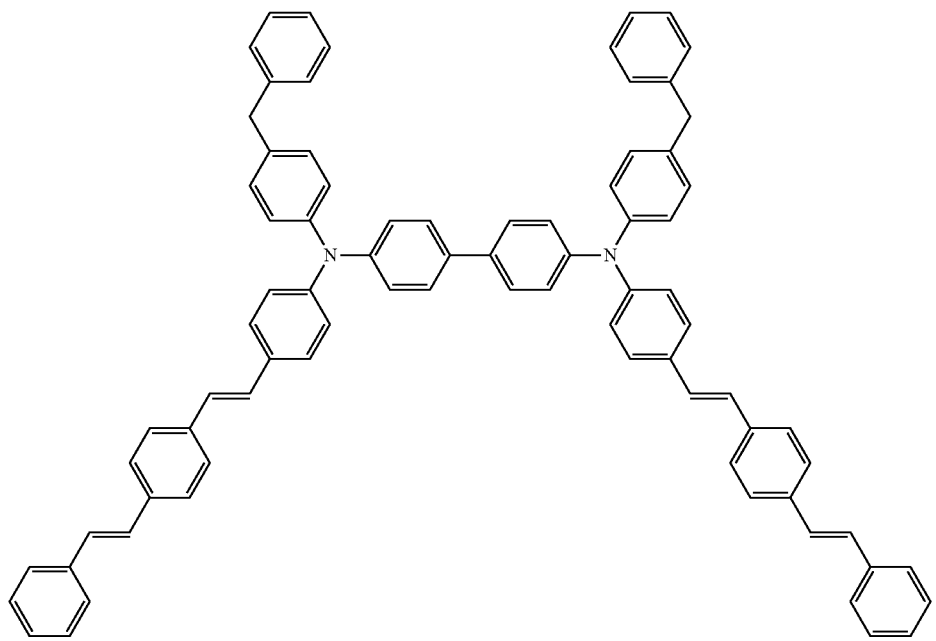
(HT-6)
* * * * *